US012618859B2

(12) United States Patent
Padmakumar et al.

(10) Patent No.: US 12,618,859 B2
(45) Date of Patent: May 5, 2026

(54) METHODS AND SYSTEMS FOR AUTOMATED SYRINGE QUALITY EVALUATION

(71) Applicant: AMGEN INC., Thousand Oaks, CA (US)

(72) Inventors: Vikashni Padmakumar, Thousand Oaks, CA (US); Evan Kruchowy, Port Hueneme, CA (US); Daniel Coller, Thousand Oaks, CA (US); Opeyemi Babatola, Oak Park, CA (US); Oscar Rosas Andrade, Los Angeles, CA (US); Gregory Evans, Westlake Village, CA (US); Stephen Flores, Sherman Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 196 days.

(21) Appl. No.: 18/287,523

(22) PCT Filed: Apr. 12, 2022

(86) PCT No.: PCT/US2022/024331
§ 371 (c)(1),
(2) Date: Oct. 19, 2023

(87) PCT Pub. No.: WO2022/225736
PCT Pub. Date: Oct. 27, 2022

(65) Prior Publication Data
US 2024/0210428 A1 Jun. 27, 2024

Related U.S. Application Data

(60) Provisional application No. 63/178,339, filed on Apr. 22, 2021.

(51) Int. Cl.
*G01N 35/00* (2006.01)
*G01N 35/04* (2006.01)
(Continued)

(52) U.S. Cl.
CPC . *G01N 35/00623* (2013.01); *G01N 35/00663* (2013.01); *G01N 35/04* (2013.01);
(Continued)

(58) Field of Classification Search
CPC ....... G01N 35/00623; G01N 35/00663; G01N 35/04; G01N 2035/00673;
(Continued)

(56) References Cited

U.S. PATENT DOCUMENTS 9,881,367 B1 * 1/2018 Milne ...................... G06T 7/11
2006/0178578 A1 8/2006 Tribble
(Continued)

FOREIGN PATENT DOCUMENTS

WO WO-2006086222 A3 4/2009
WO WO-2019032101 A1 2/2019
WO WO-2019103847 A1 5/2019

OTHER PUBLICATIONS

International Search Report for Application No. PCT/US2022/024331 dated Sep. 2, 2022.
(Continued)

*Primary Examiner* — Paul M. West
(74) *Attorney, Agent, or Firm* — MARSHALL, GERSTEIN & BORUN LLP; Michael P. Furmanek

(57) ABSTRACT

Automatic syringe quality control systems, apparatus and methods are provided. The automatic syringe quality control systems, apparatus and methods may determine a plunger
(Continued)

depth within a syringe that has been pre-filled with a medication. The plunger depth may be based on digital image data.

14 Claims, 25 Drawing Sheets

(51) Int. Cl.

| | | |
|---|---|---|
| *G06T 7/00* | (2017.01) | |
| *G06T 7/50* | (2017.01) | |
| *A61M 5/31* | (2006.01) | |
| *A61M 5/315* | (2006.01) | |

(52) U.S. Cl.
CPC .............. *G06T 7/0004* (2013.01); *G06T 7/50* (2017.01); *A61M 5/3129* (2013.01); *A61M 5/31511* (2013.01); *G01N 2035/00673* (2013.01); *G01N 2035/0491* (2013.01); *G06T 2207/30108* (2013.01)

(58) Field of Classification Search
CPC .... G01N 2035/0491; G01N 2035/0493; G06T 7/50; G06T 7/70; G06T 7/73; G06T 7/74; G06T 7/75; G06T 7/0004
See application file for complete search history.

(56) References Cited

U.S. PATENT DOCUMENTS

| | | |
|---|---|---|
| 2009/0188311 A1 | 7/2009 | Cadieux et al. |
| 2013/0000250 A1 | 1/2013 | Tribble et al. |
| 2016/0001003 A1 | 1/2016 | Perazzo et al. |
| 2018/0051243 A1 | 2/2018 | Hogan et al. |
| 2018/0154088 A1 | 6/2018 | Broselow |
| 2019/0156697 A1 | 5/2019 | Trovato et al. |

OTHER PUBLICATIONS

Written Opinion for Application No. PCT/US2022/024331 dated Sep. 2, 2022.
Eurasian Patent Application No. 202492214, Search Report, dated Aug. 8, 2024.
Japanese Patent Application No. 2023562211, Notice of Reasons for Refusal, dated Jan. 6, 2026.

* cited by examiner

| No. | Plunger Depth |
|---|---|
| 1. | 10.52 mm |
| 2. | 10.54 mm |
| 3. | 10.53 mm |
| 4. | 10.54 mm |
| 5. | 10.44 mm |
| 6. | 10.59 mm |
| 7. | 10.49 mm |

300a

352a

352a

351a

350a

300b

353b

354b

354b

355b

355b

| No. | Plunger Depth |
|-----|---------------|
| 1.  | 10.52 mm      |
| 2.  | 10.54 mm      |
| 3.  | 10.53 mm      |
| 4.  | 10.54 mm      |
| 5.  | 10.44 mm      |
| 6.  | 10.59 mm      |
| 7.  | 10.49 mm      |

METHODS AND SYSTEMS FOR AUTOMATED SYRINGE QUALITY EVALUATION

CROSS-REFERENCE TO RELATED APPLICATION

This is the United States national phase of International Patent Application No. PCT/US2022/024331, filed Apr. 12, 2022, which claims priority to U.S. Provisional Patent Application No. 63/178,339, filed Apr. 22, 2021, the entire contents of each of which are hereby incorporated by reference herein.

FIELD OF DISCLOSURE

The present disclosure relates to syringe manufacturing and quality control and, more particularly to methods and apparatus for automated syringe quality control imaging.

BACKGROUND

Numerous drug products are manufactured and stored in syringes and manufactured to the highest quality standards. Some drug products include pre-filled syringes having pre-measured doses of drugs stored within the syringe barrel. Properly manufactured pre-filled syringes have unique plunger depth requirements. The plunger depth is unique based on the drug, container, and fill volume. Thus, for a given drug, container, and fill volume, how deep the plunger is disposed in the syringe barrel is a controlled variable.

Because the plunger depth is a controlled variable for all pre-filled syringe cartridges, one aspect of the quality control process is verifying the depth of plungers in manufactured syringes. Currently, the plunger depth is manually measured by lab technicians using calipers. If the plunger depth does not match the plunger depth corresponding to the unique drug product, the syringe fails this quality control process.

SUMMARY

An automatic syringe measurement system may include an imaging system capable of generating imaging data. The imaging system may include a camera, an imaging surface, and an illumination source. The automatic syringe measurement system may also include an alignment device for aligning at least one syringe relative the imaging system. The automatic syringe measurement system may further include a processor configured to receive the imaging data from the imaging system, and determine whether a depth of a plunger within a barrel of at least one syringe is within a predetermined tolerance.

In another embodiment, syringe carrying tub assembly may include a tub configured to receive a plurality of syringes. The syringe carrying tub assembly may also include a syringe carrier plate have a plurality of apertures extending from a top surface of the syringe carrier plate to a bottom surface of the syringe carrier plate. Each of the plurality of apertures may be configured to receive one of a plurality of syringes. The syringe carrying tub assembly may further include a tub insert configured to be placed within the tub prior to the plurality of syringes being placed into the tub. The tub insert may include at least one syringe elevator aligned with at least one of the plurality of syringes. When the syringe carrier plate, the tub insert, and the plurality of syringes are placed within the tub, the at least one syringe elevator may be configured to elevate the at least one syringe configured to be received in the at least one aperture aligned with the syringe elevator relative to the remaining syringes of the plurality of syringes.

In a further embodiment, a syringe removal tool may include a syringe carrier having a first end, a second end, and a plurality of syringe receptacles linearly arranged along an edge of the syringe carrier from the first end to the second end. The syringe removal tool may also include a stationary grip portion having a first end and a send end. The first end of the syringe carrier may be connected to the first end of the stationary grip portion via a first slide rod. The second end of the syringe carrier may be connected to the second end of the stationary grip portion via a second slide rod. The syringe removal tool may further include a syringe retainer portion having a first end, a second end, and a plurality of spring biased syringe retainers linearly arranged along the syringe retainer portion from the first end to the second end. Each spring biased syringe retainer may be configured to retain a respective syringe within a respective syringe receptacle independent of any other spring biased syringe retainer in the plurality of spring biased syringe retainers. The first end of the syringe retainer portion may be configured to slide along the first slide rod. The first end of the syringe retainer portion may be biased toward the first end of the syringe carrier portion via a first syringe retainer portion bias spring. The second end of the syringe retainer portion may be configured to slide along the second slide rod. The second end of the syringe retainer portion may be biased toward the second end of the syringe carrier portion via a second syringe retainer portion bias spring.

In yet another embodiment, a syringe rack may include a plurality of syringe receptacles. At least one syringe receptacle may include an open end defining a syringe barrel receptacle. The syringe barrel receptacle may be configured to receive a syringe barrel. Each syringe receptacle may be configured to align a respective syringe in a pre-determined orientation relative the syringe rack.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicated of the presence or absence of particular elements in any of the exemplary embodiments, except as may be explicitly delineated in the corresponding written description. Also, none of the drawings are necessarily to scale.

3

Figure 2A:
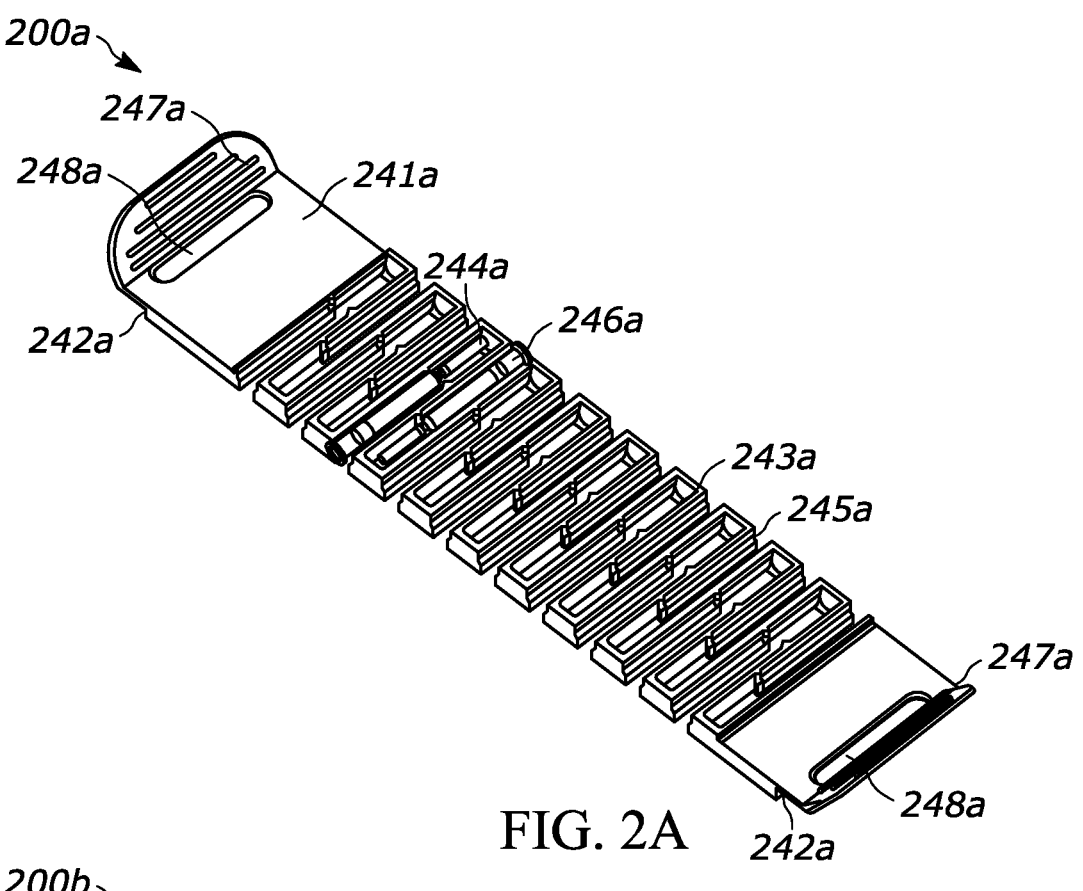
FIG. 2A depicts a perspective view of an example alignment rack.
Figure 2B:
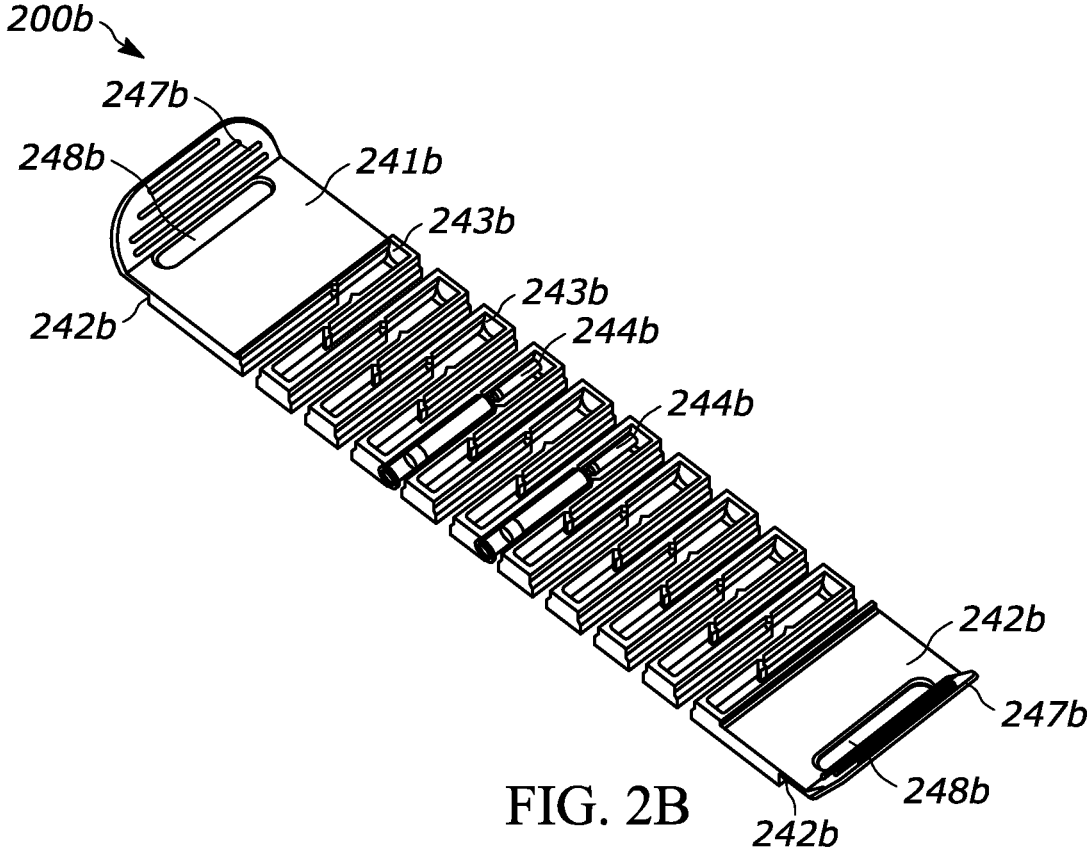
FIG. 2B depicts a perspective view of an example alignment rack.
Figure 2C:
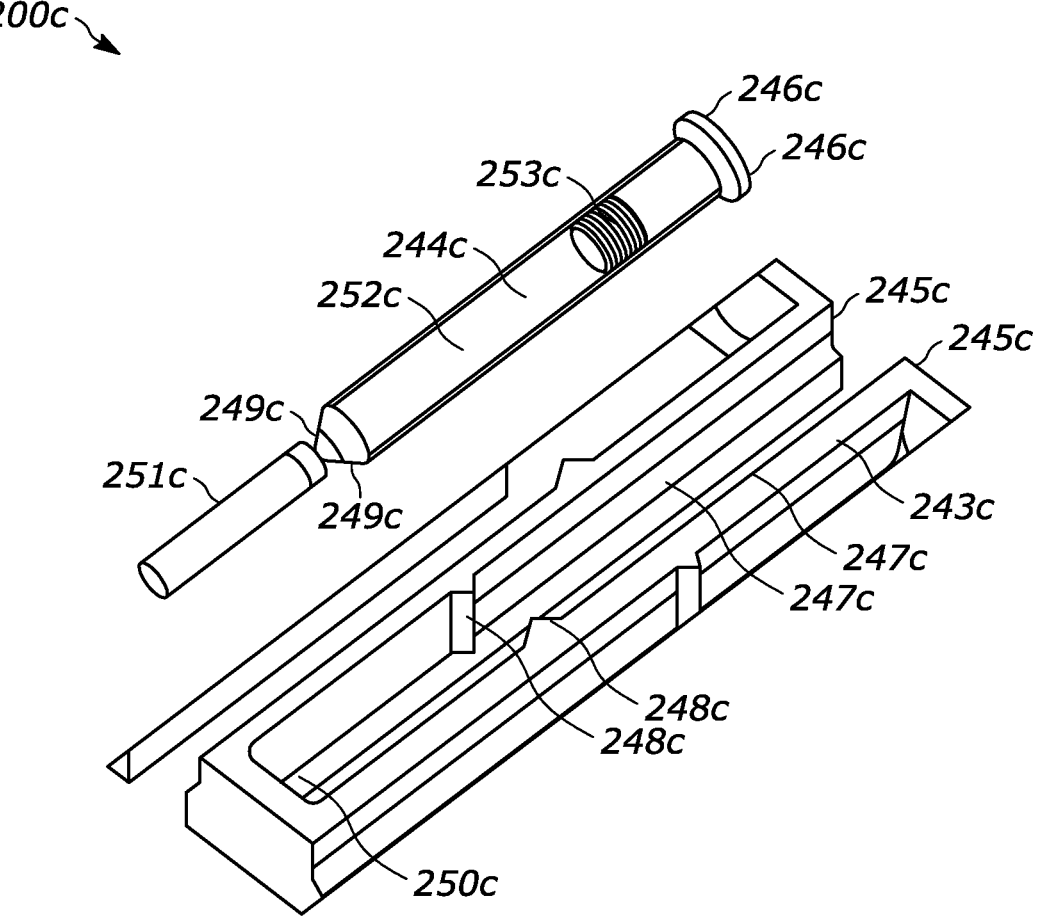
Figure 3A:
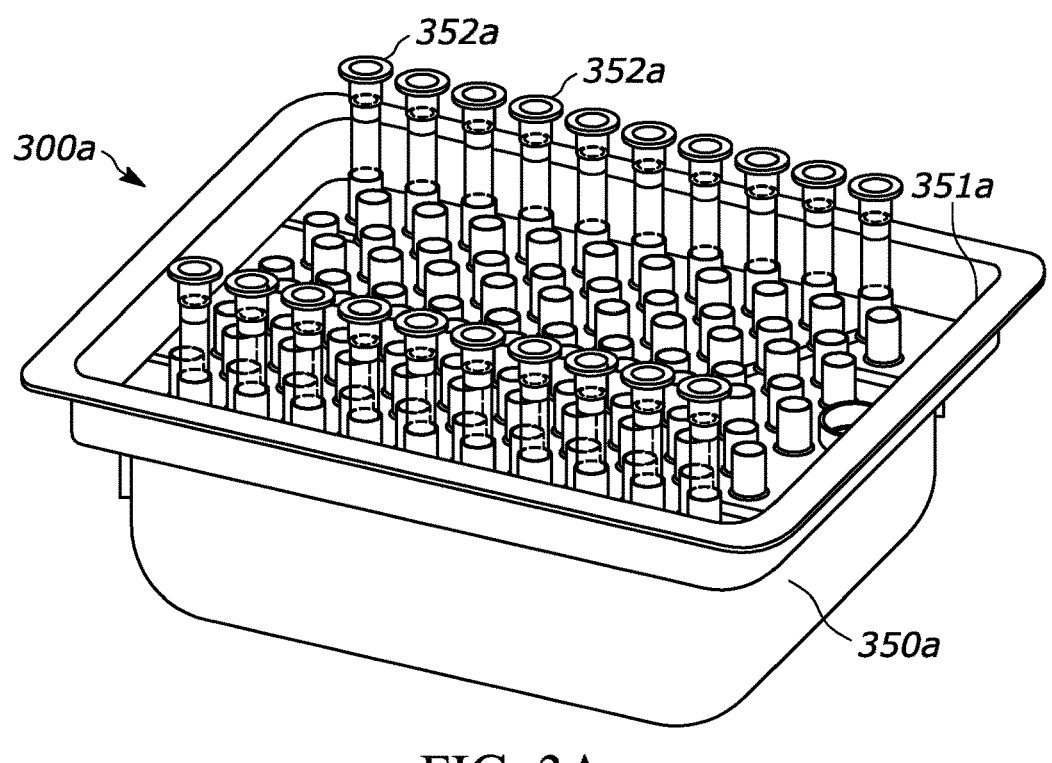
Figure 3B:
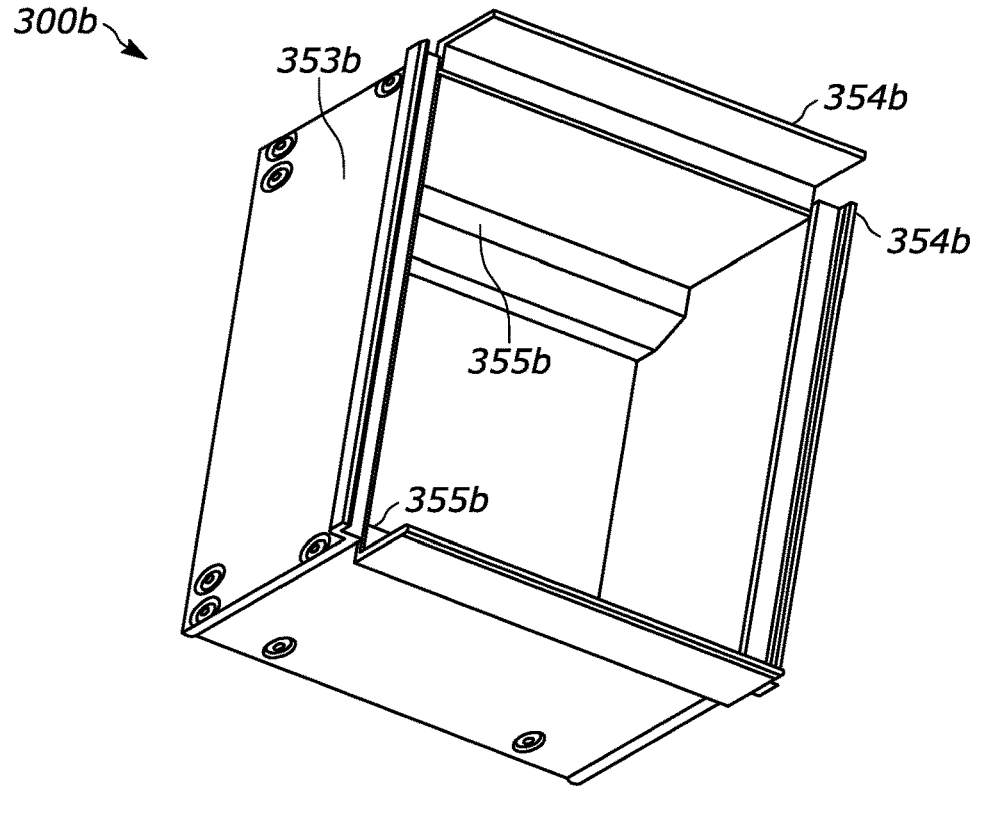
Figure 4A:
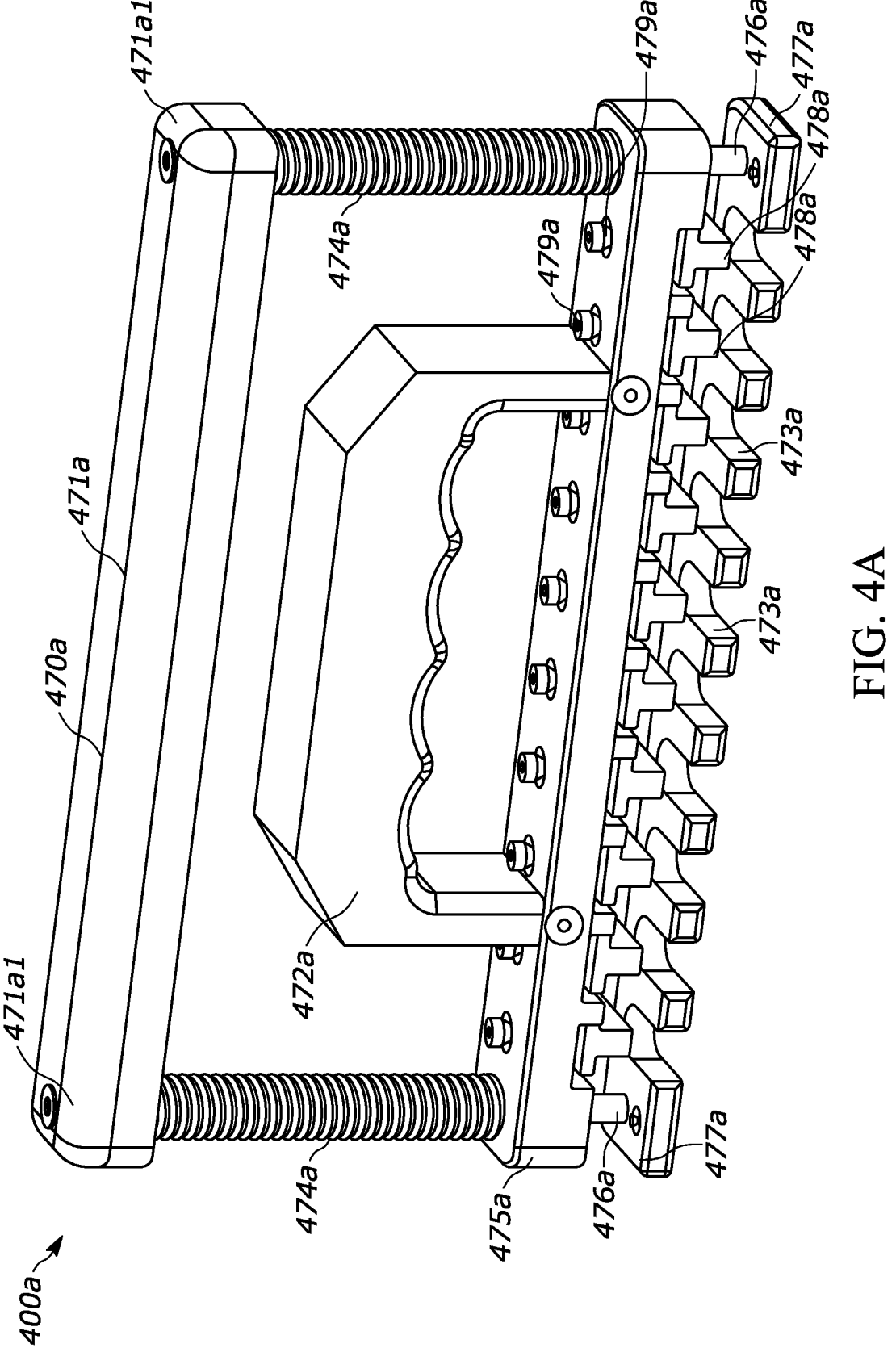
Figure 4B:
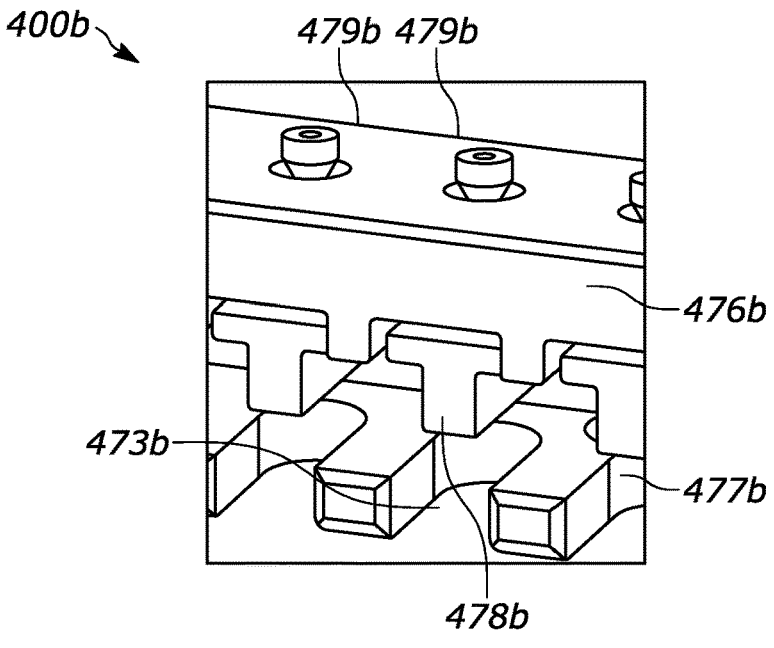
Figure 4B:
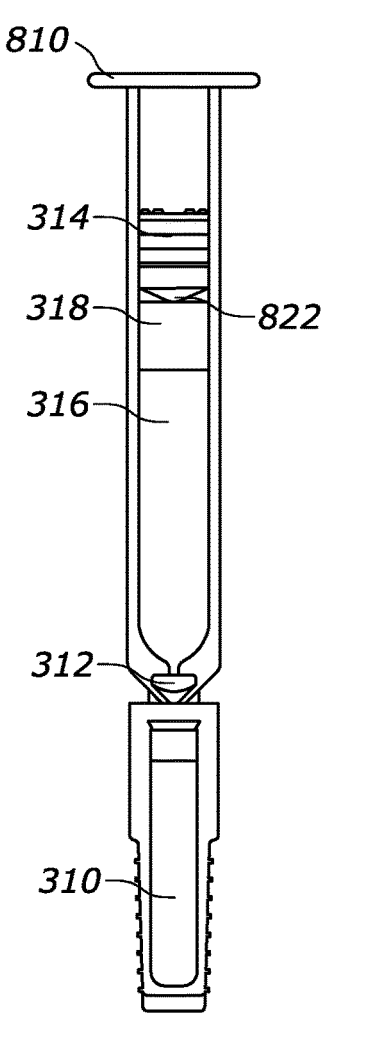
Figure 4C:
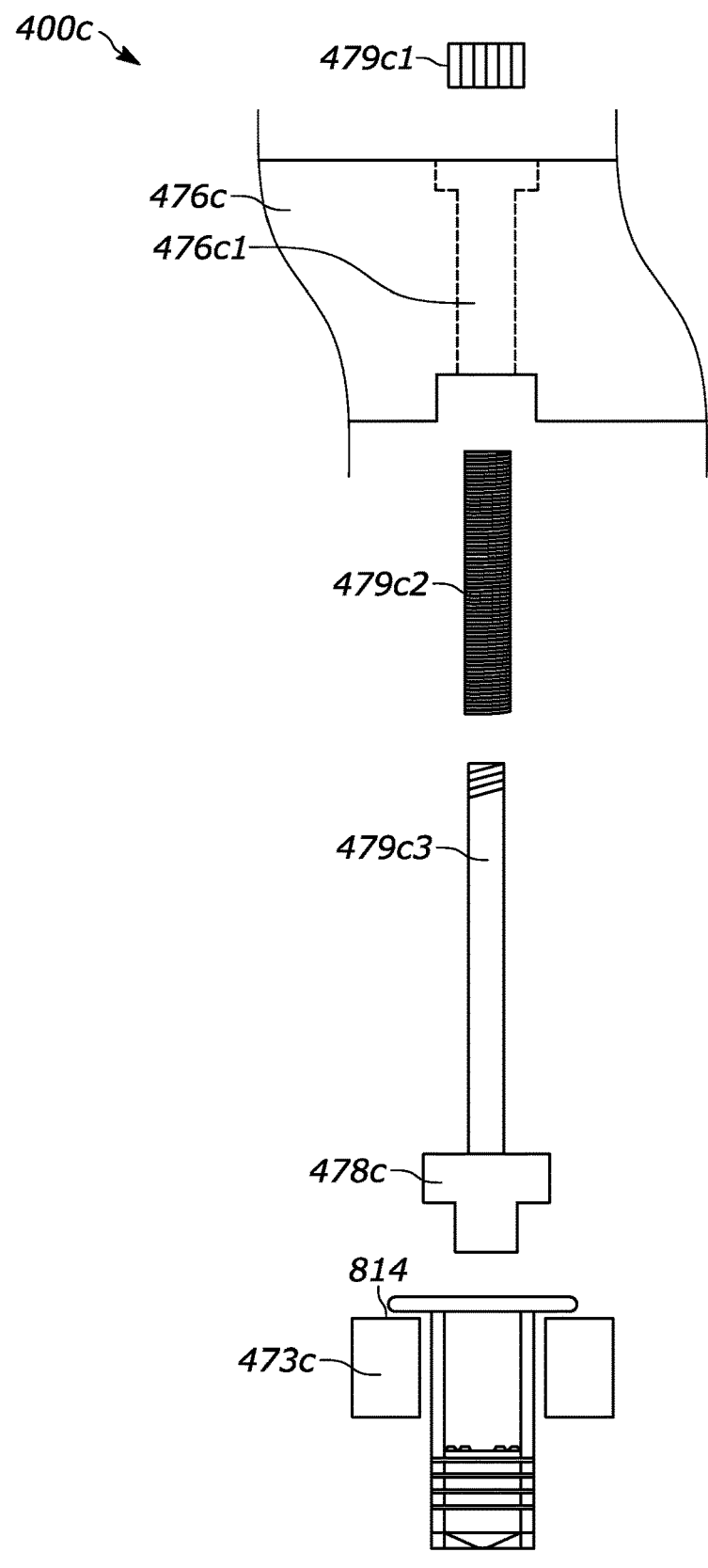
Figure 4D:
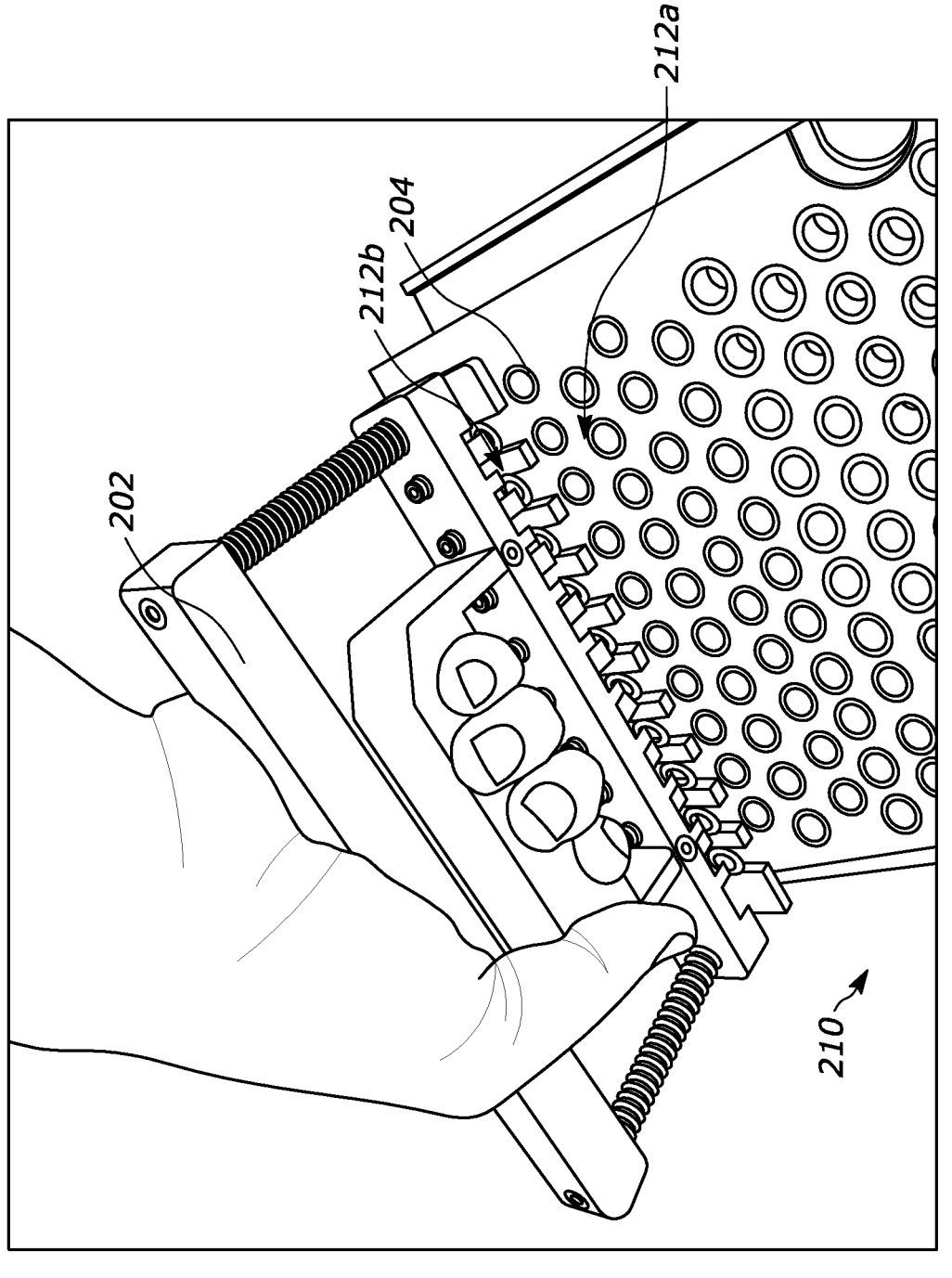
Figure 4E:
Figure 4E:
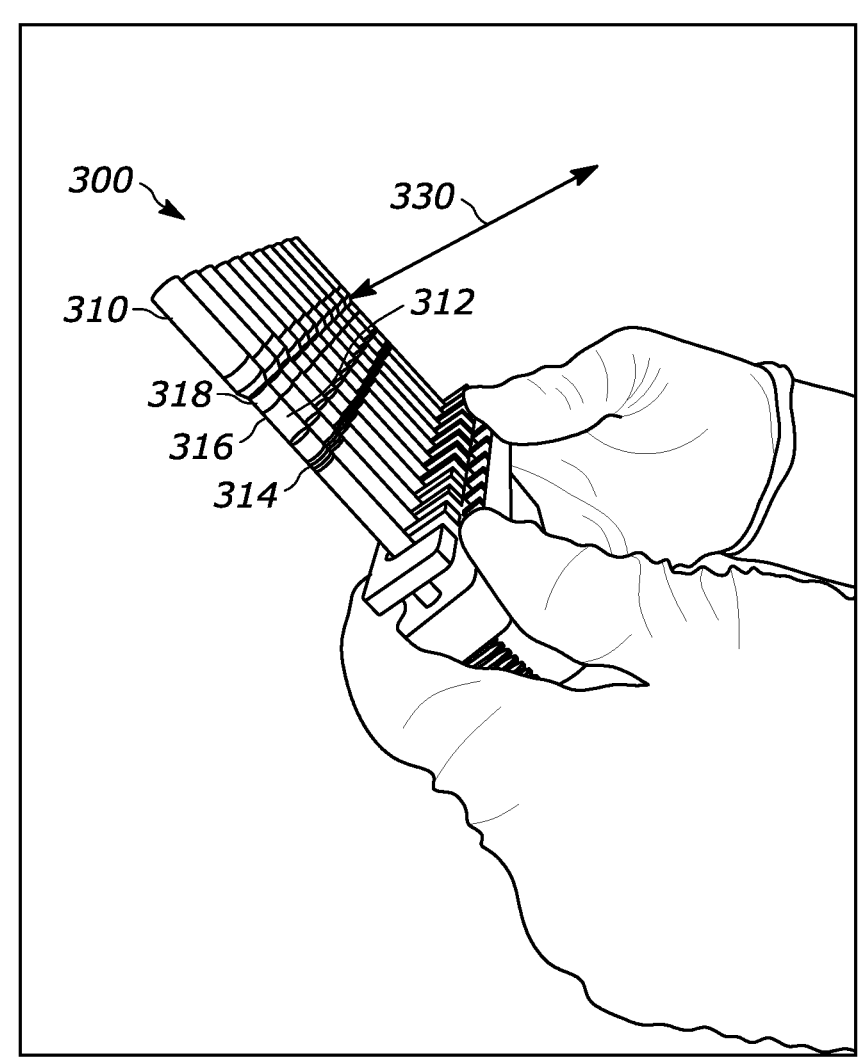
Figure 4F:
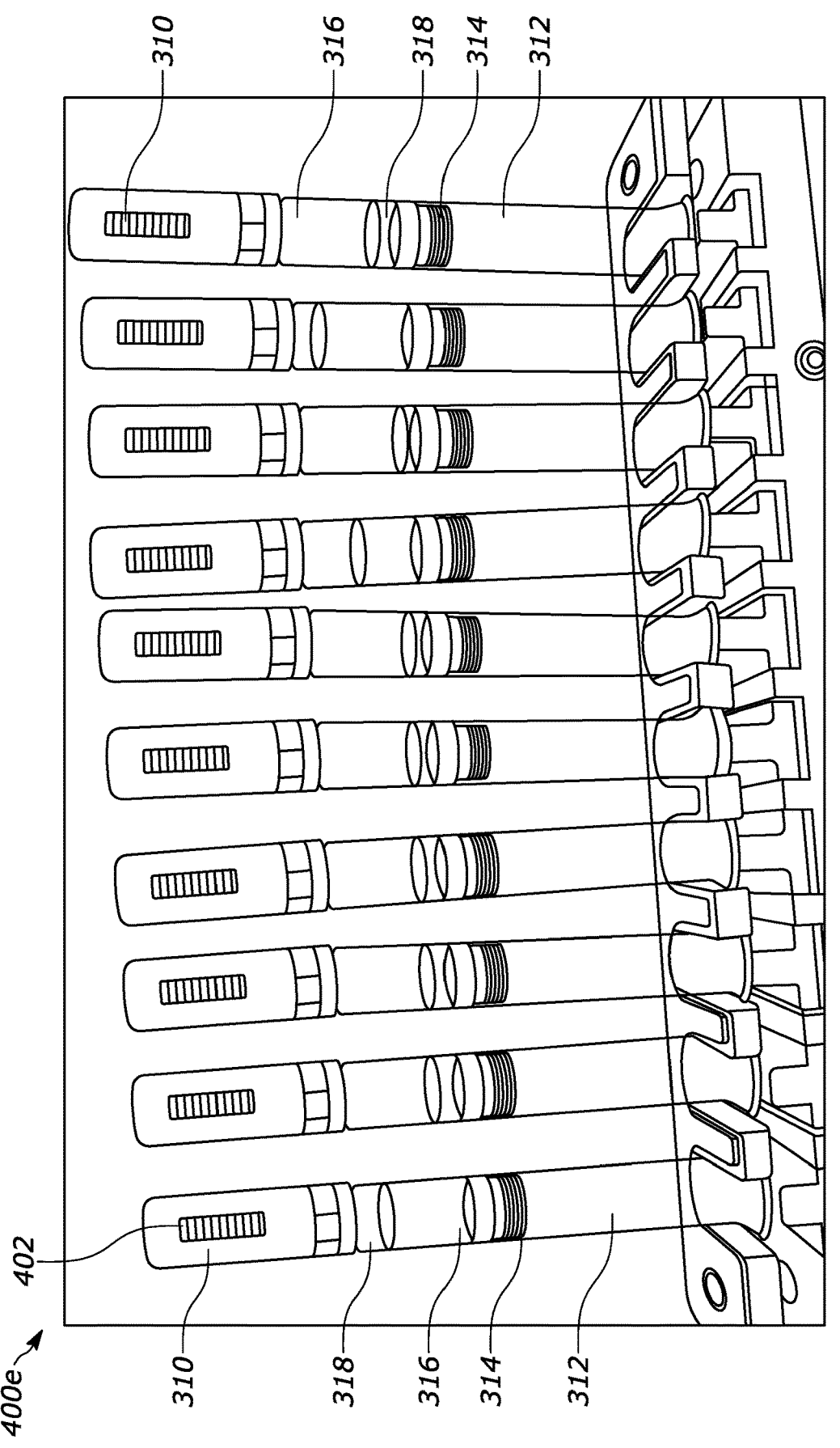
Figure 4G:
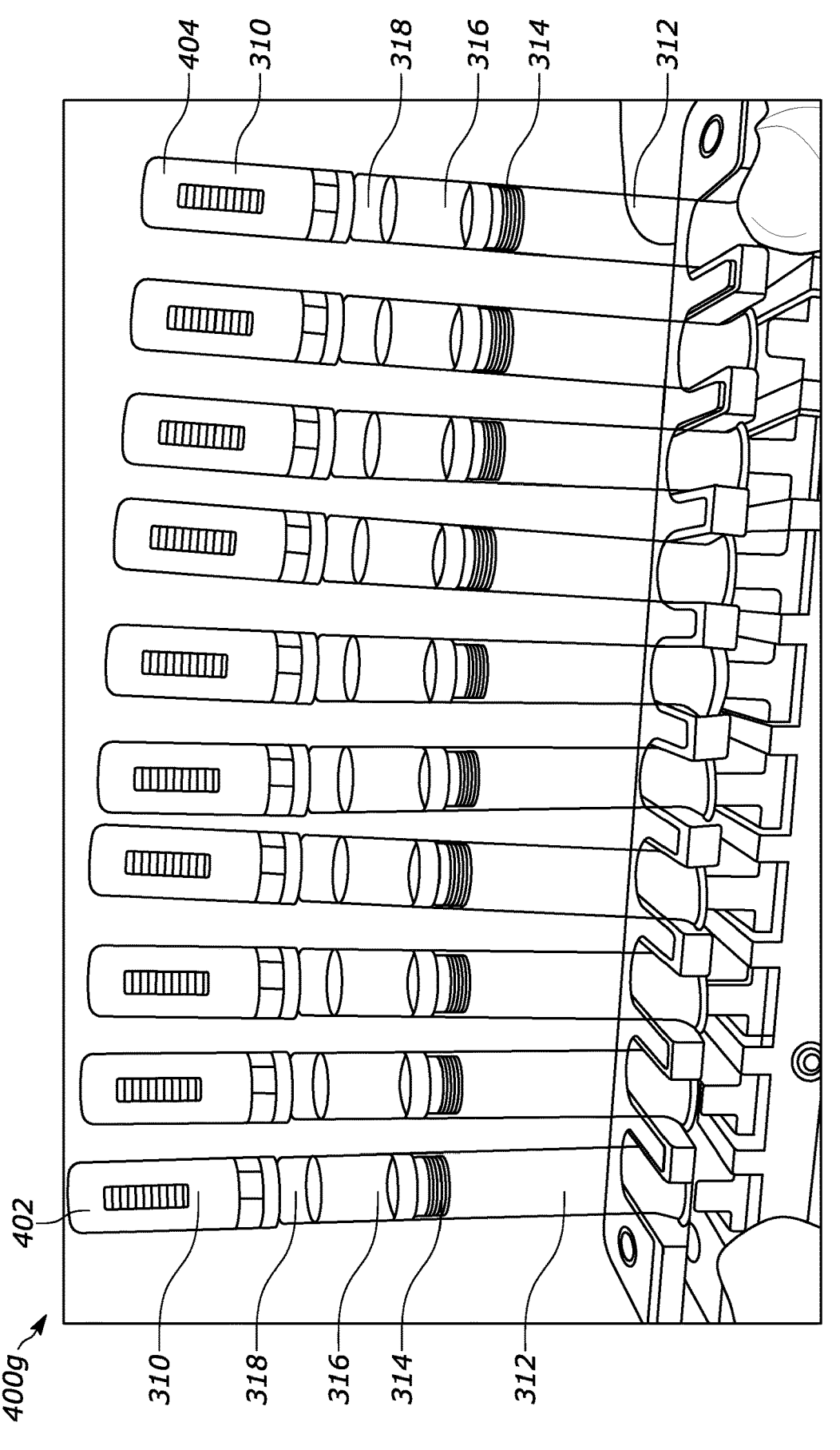
Figures 5, 6A:
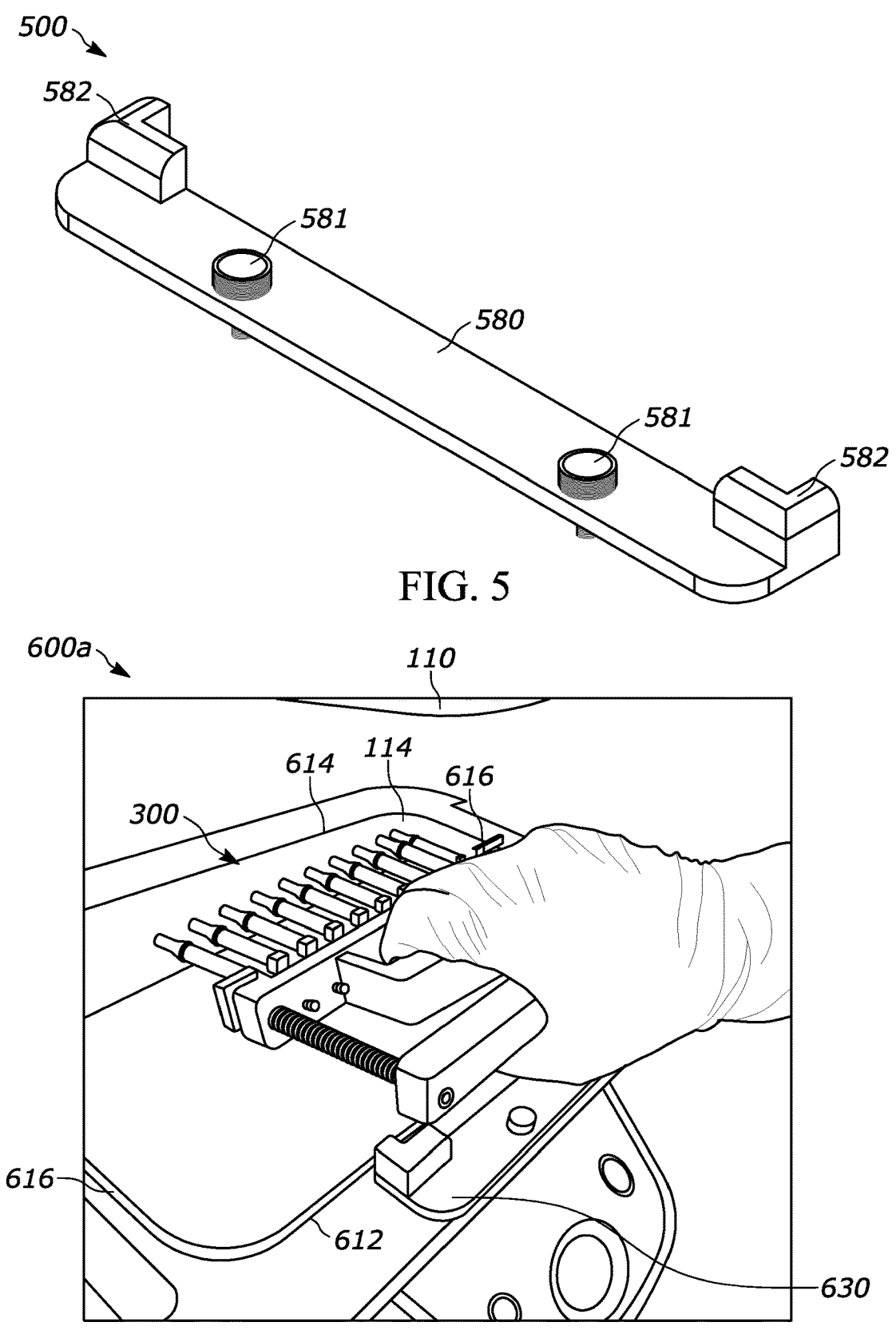
Figure 6B:
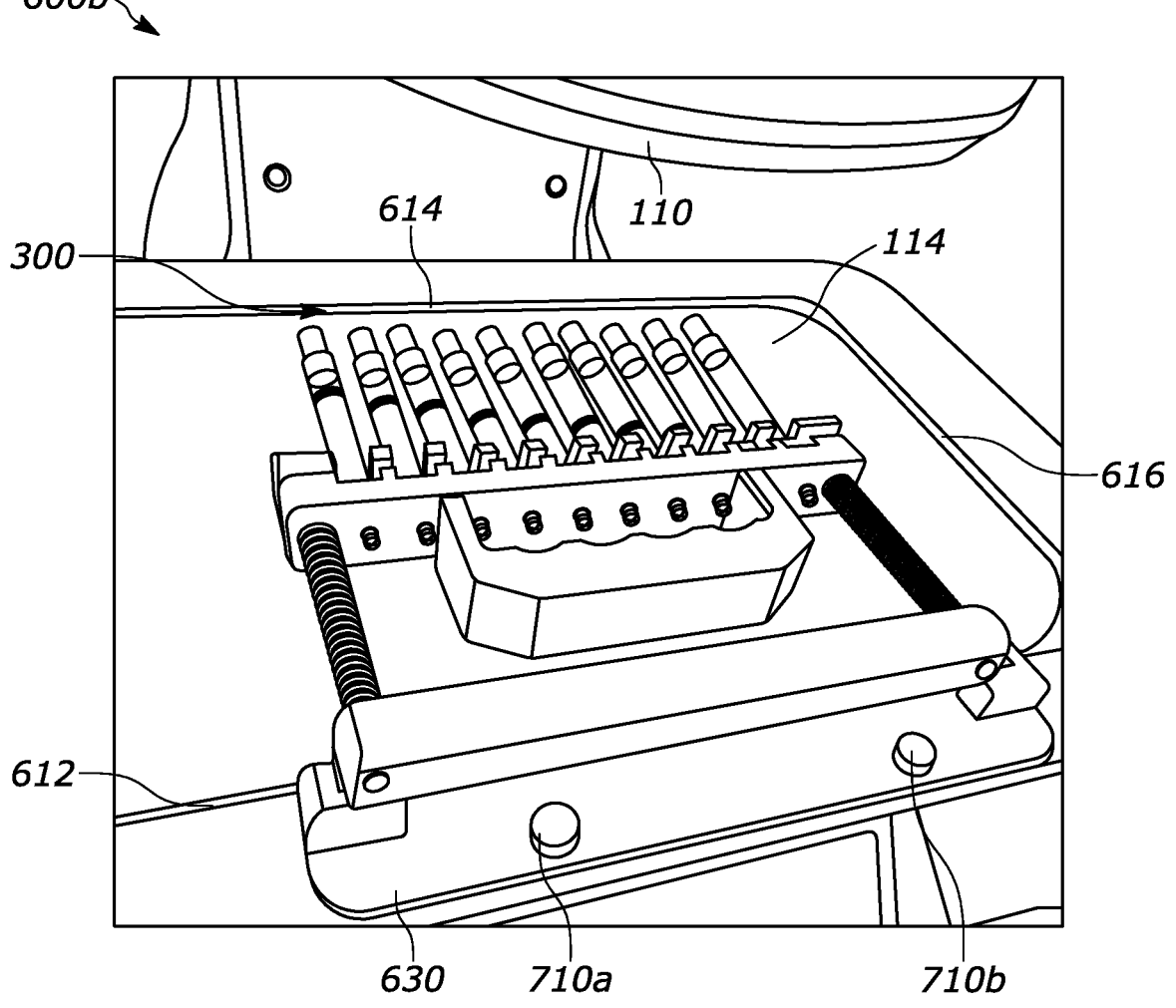
Figure 7A:
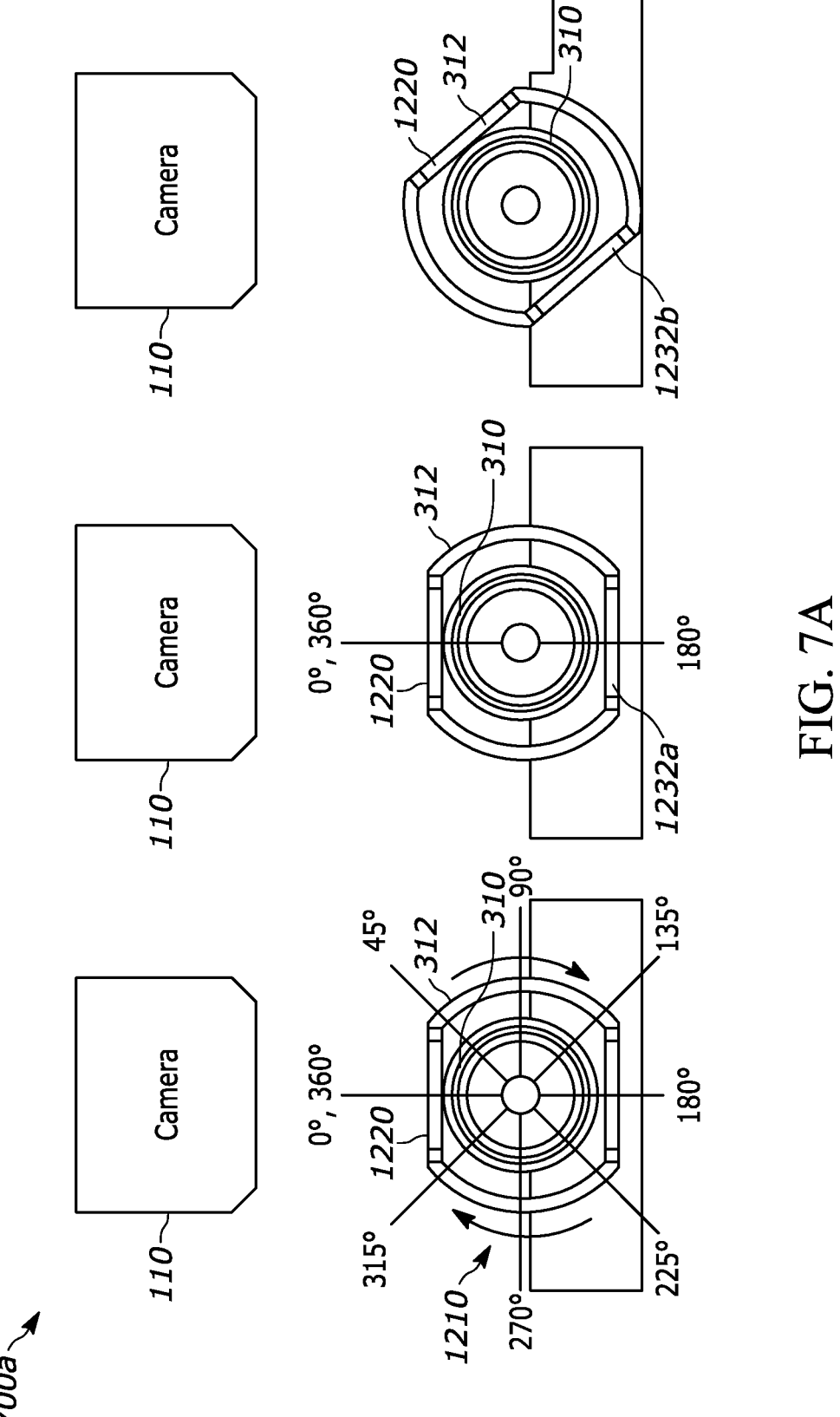
Figure 7B:
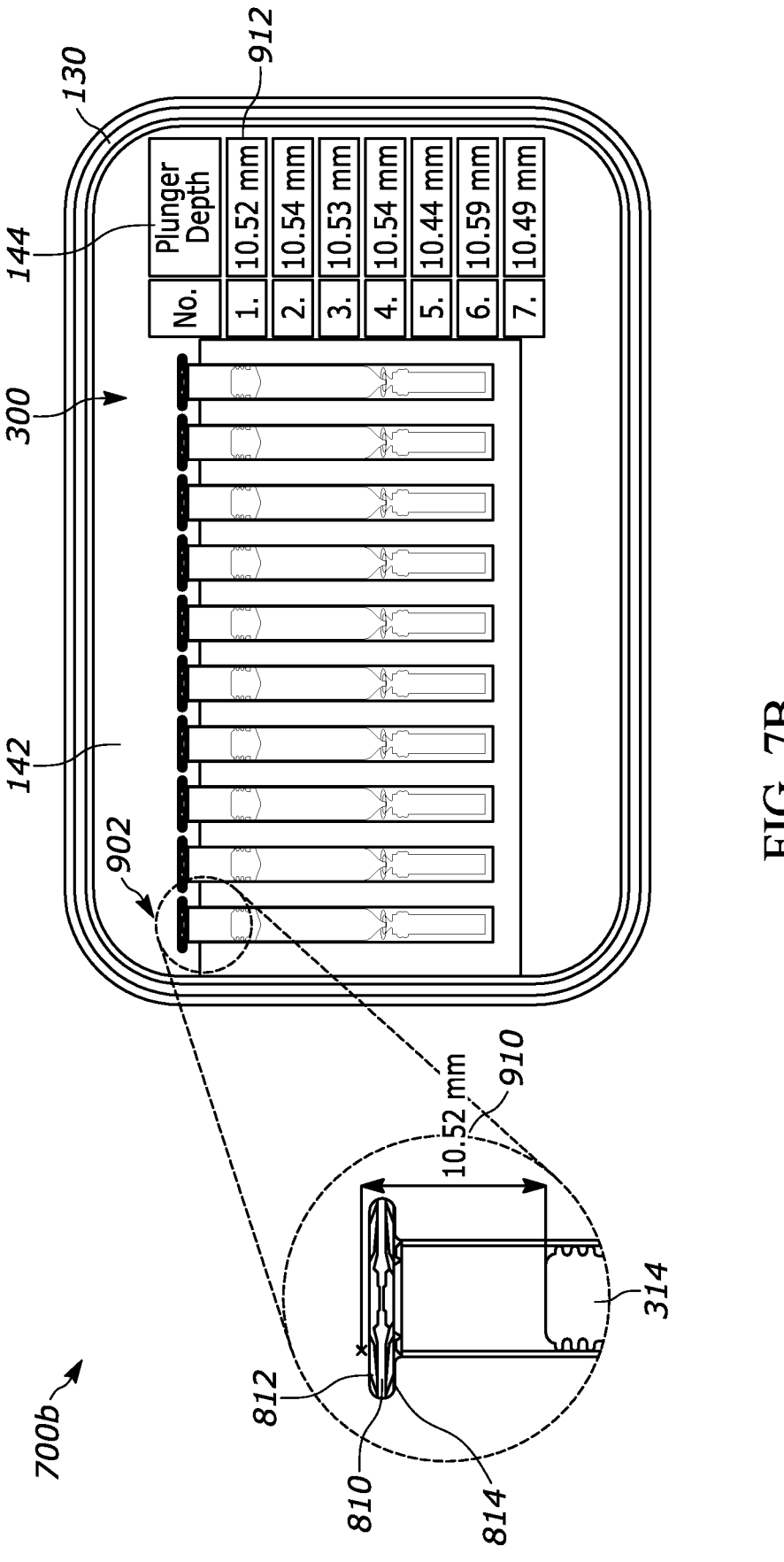
Figure 7C:
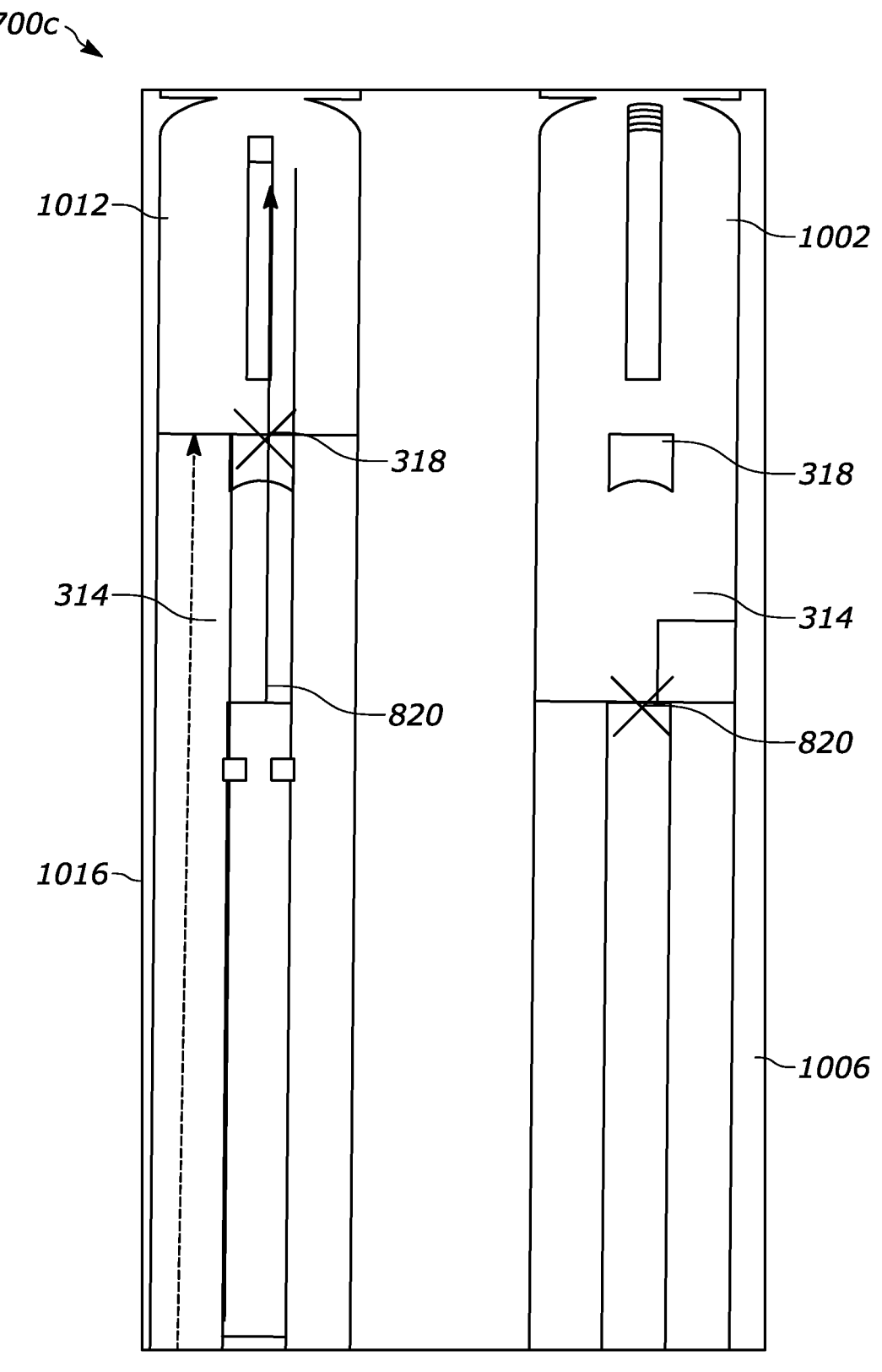
Figure 7D:
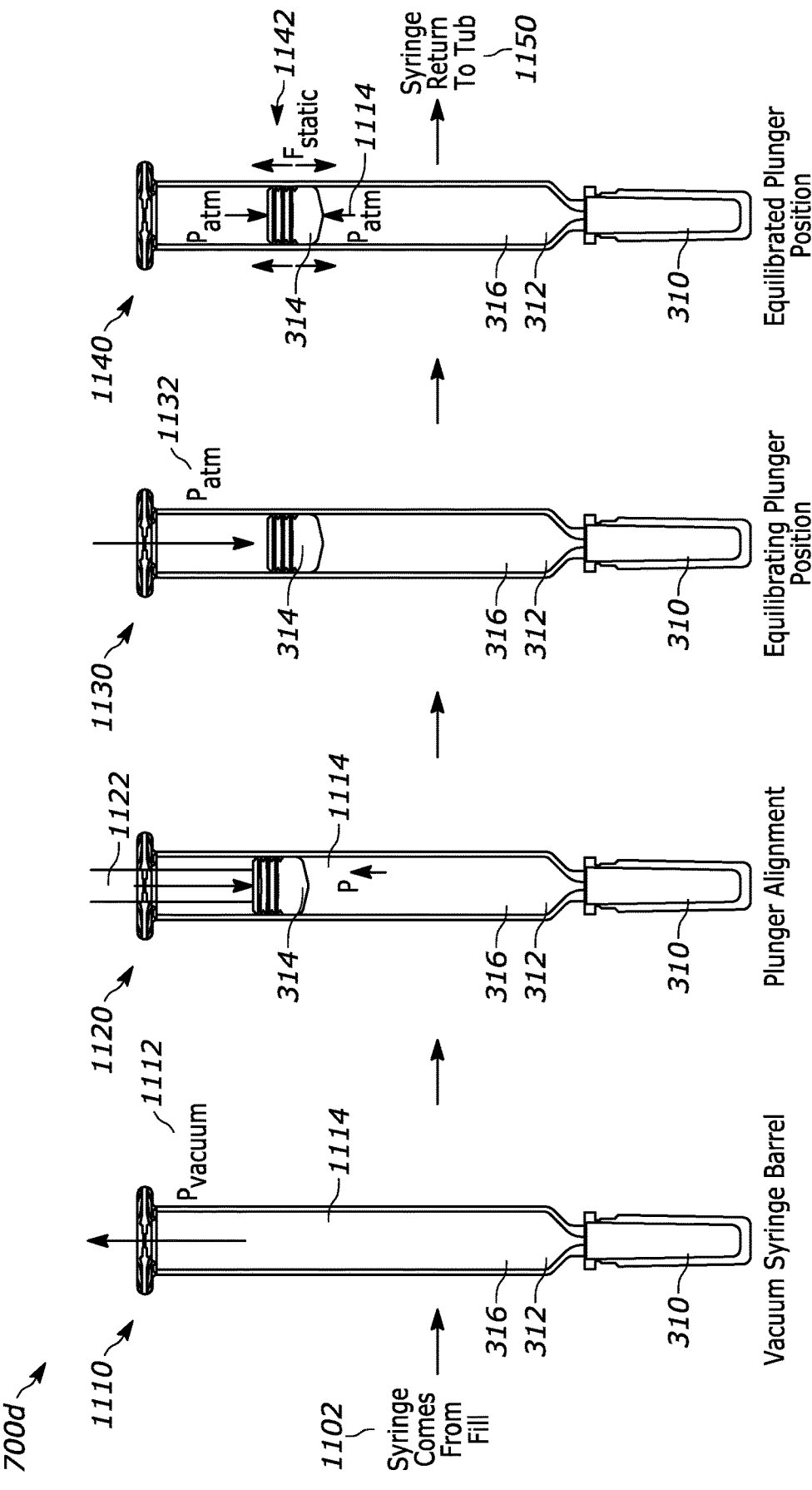
Figure 7E:
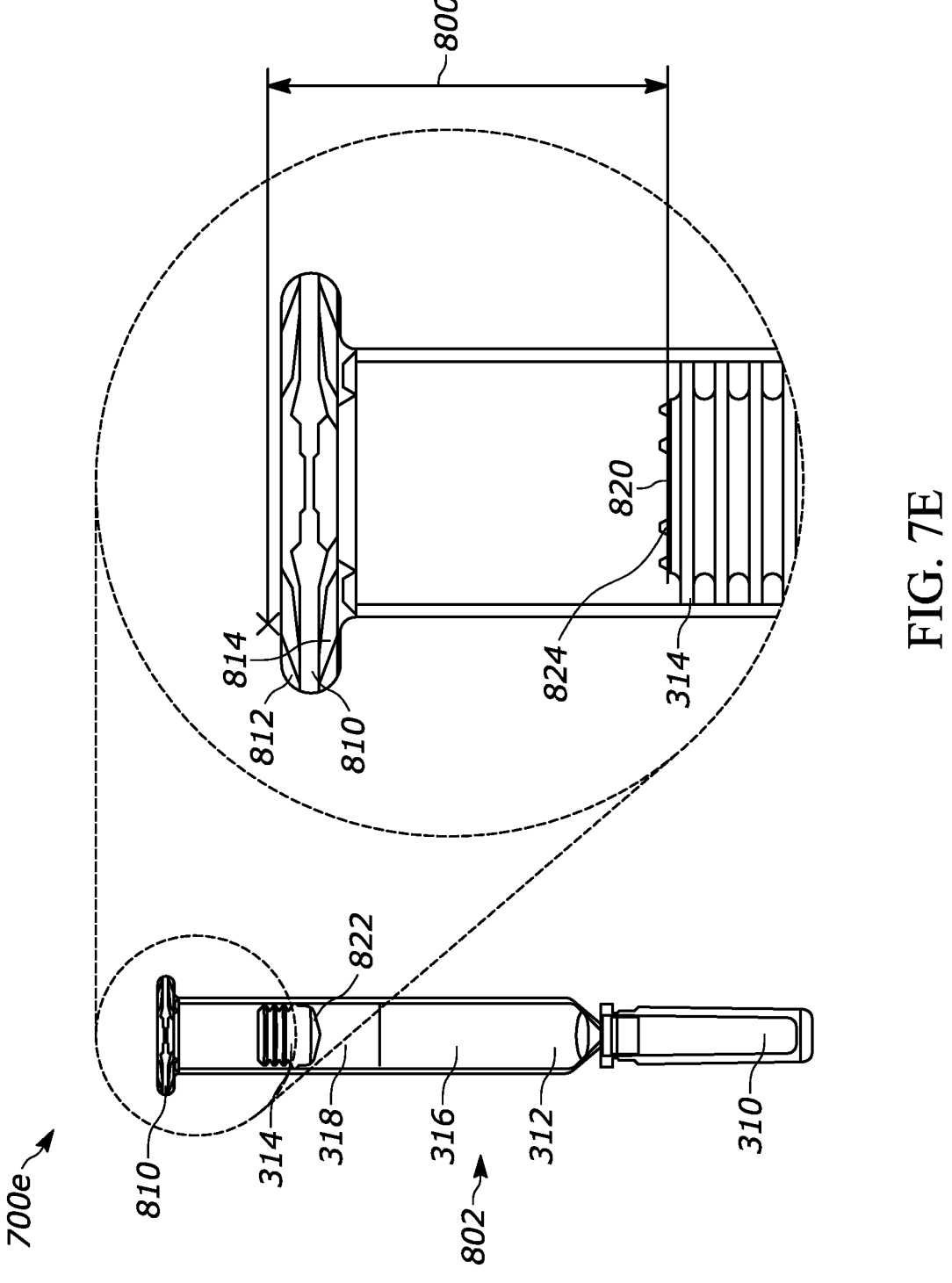
Figures 8A, 8B:
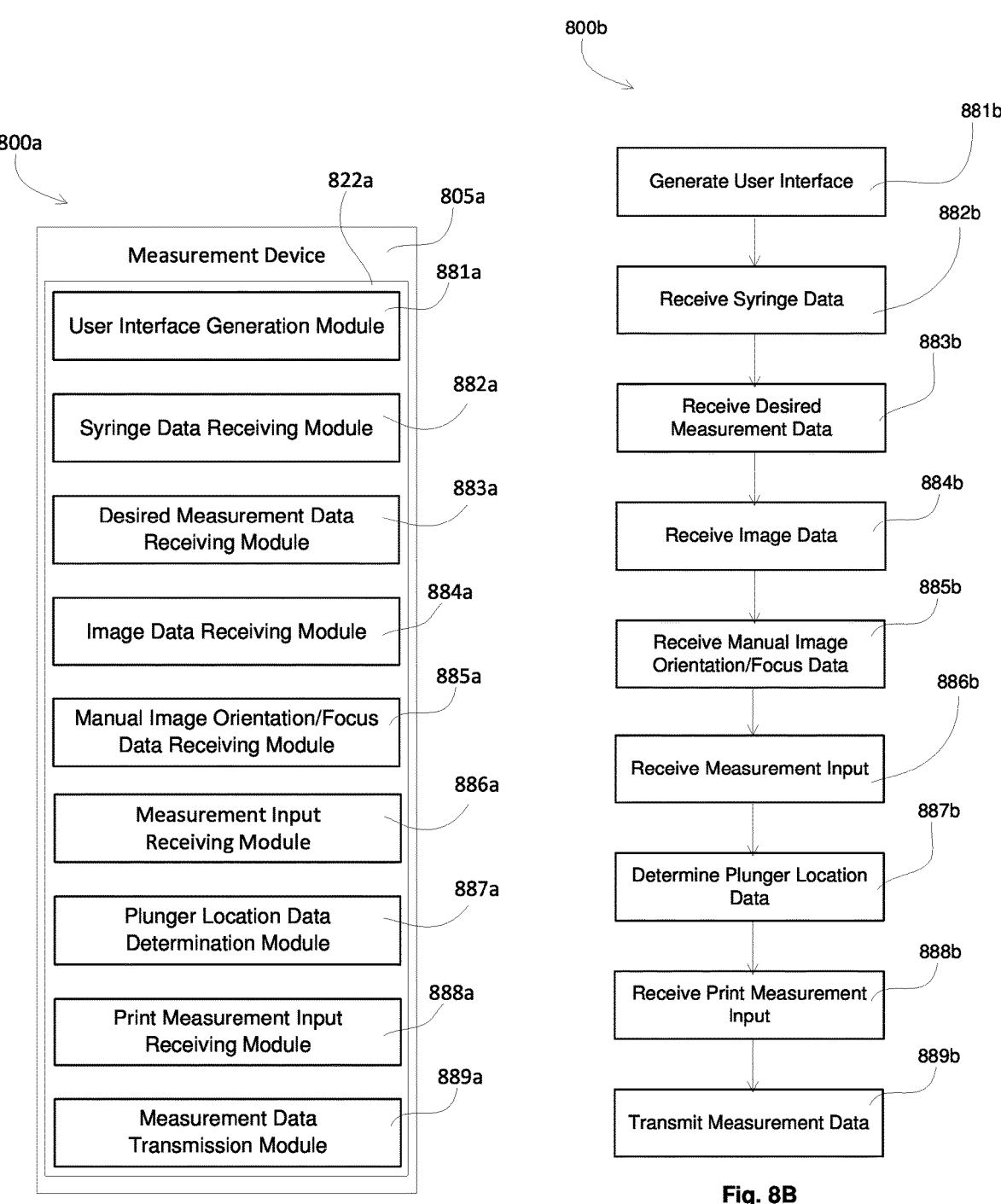
Figures 9A, 9B:
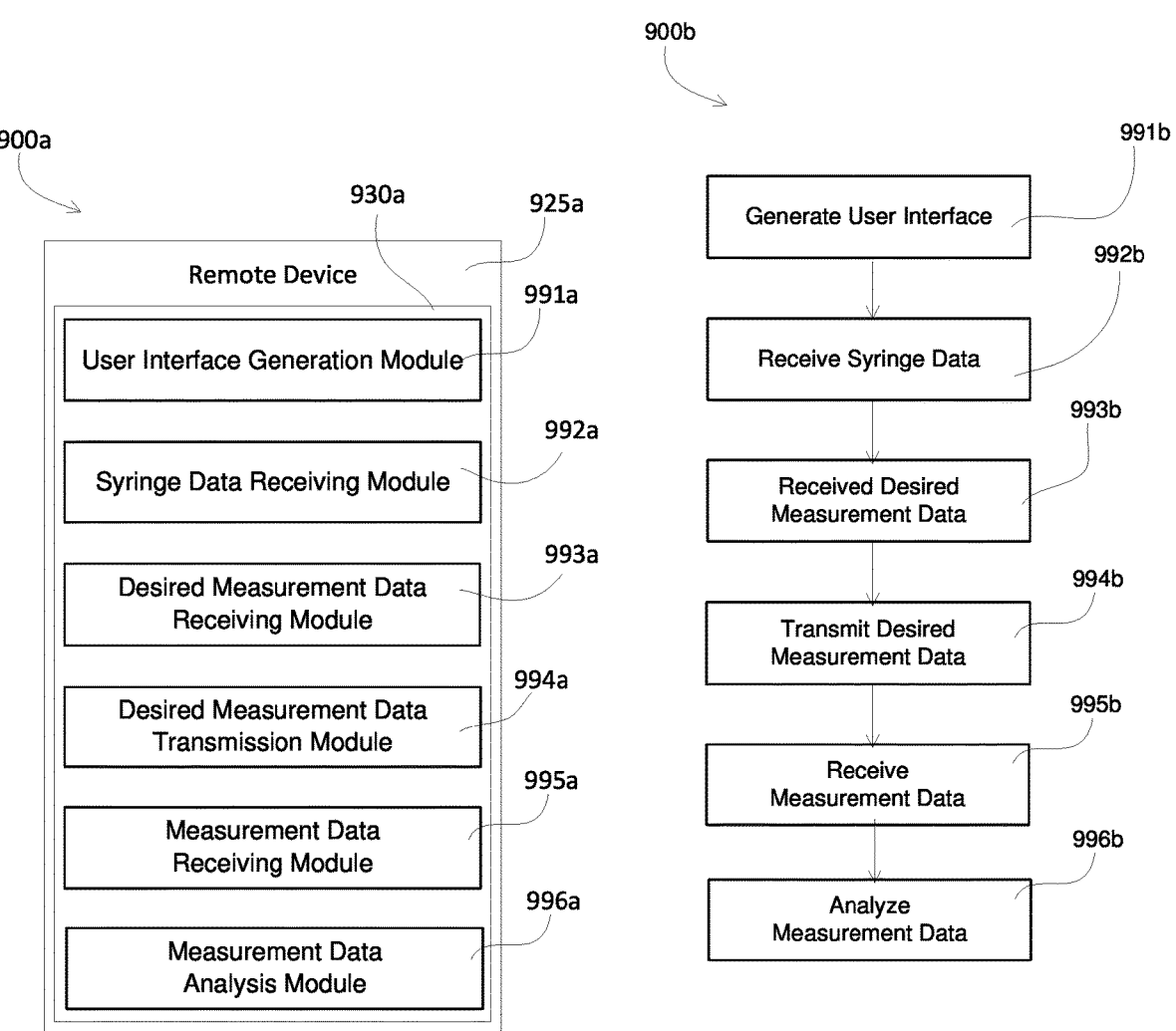

FIG. 2C depicts a perspective view of a portion of an example alignment rack in relation with a respective syringe;

FIG. 3A depicts a perspective view of an example tub full of syringes;

FIG. 3B depicts a perspective view of an example tub insert;

FIG. 4A depicts a perspective view of an example syringe removal tool;

FIG. 4B depicts a perspective view of a portion of an example syringe removal tool in relation with a respective syringe;

FIG. 4C depicts a profile view of an exploded portion of an example syringe removal tool in operable relation with a respective portion of a syringe;

FIG. 4D depicts a perspective views of an example syringe removal tool in operable relation with a tub of syringes;

FIG. 4E depicts a perspective view of a plurality of example syringes;

FIG. 4F depicts an example side view of a plurality of example syringes;

FIG. 4G depicts an example side view of a plurality of syringes;

FIG. 5 depicts a perspective view of an example imaging device syringe alignment adapter;

FIG. 6A depicts a perspective view of a plurality of example syringes being placed on an imaging surface of an example imaging device;

FIG. 6B depicts a perspective view of a plurality of example syringes aligned on an imaging surface of an example imaging device;

FIG. 7A depicts a side view of example syringe alignment relative a camera;

FIG. 7B depicts an example display of plunger depth measurements of the plurality of syringes;

FIG. 7C depicts an example display of a correct and incorrect plunger depth measurement;

FIG. 7D depicts an example method of syringe plunger insertion and equilibration;

FIG. 7E depicts a side view of an example plunger depth measurement;

FIG. 8A depicts a block diagram of an example measurement device;

FIG. 8B depicts an example method of operating a measurement device;

FIG. 9A depicts a block diagram of a remote computing device for use in a syringe inspection system; and FIG. 9B depicts an example method of operating a remote computing device for use in a syringe inspection system.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercial feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Some quality control processes for pre-filled syringes (e.g., pre-filled 1 mL syringes, pre-filled 0.5 mL (Terumo) syringes, products, pre-filled 2.25 mL syringes, 5 mL cartridges, etc.) are currently handled manually by technicians. For example, one quality control process for pre-filled syringes involves measuring the depth the plunger is inserted in the syringe barrel. The depth of the plunger in the syringe barrel is unique for each given drug product based on the drug, container, and fill volume. As a result, for a given drug product, if the plunger is at an incorrect depth, the syringe fails quality control. And currently, the depth of the plunger is typically measured manually with calipers. As often used in the context of drug delivery a "distal" end of a syringe is generally meant herein as being away from a patient, and "proximal" as toward the patient.

In accordance with the present disclosure, the syringe plungers may be imaged, and a plunger depth may be measured using digital image data that is representative of the image of the syringe. For example, a plurality of syringes can be imaged by a camera and a processor can measure a plurality of syringes at the same time. In such an example, the syringes can be placed on a imaging surface of a measurement device to align a plurality of syringes. The syringes may then be appropriately illuminated, and an image may be taken of the illuminated syringes. A processor can then measure the depth of at least one plunger in a respective syringe based on the image data. As a result, instead of manually measuring the depth of each plunger, multiple syringes can be measured simultaneously and more accurately than before.

Automated syringe measurement systems are generally more precise and accurate than manual measurement methods. Additionally, using the automated syringe measurement system can automatically and securely record quality data and batch numbers. Further, the automated syringe measurement system processes more syringes per minute than manual measurement techniques. And also, some automated systems in accordance with the present disclosure require fewer operating personnel. As a result, the automated syringe measurement system of the present disclosure can be better than the current manual syringe quality control procedures.

Figure 1A:
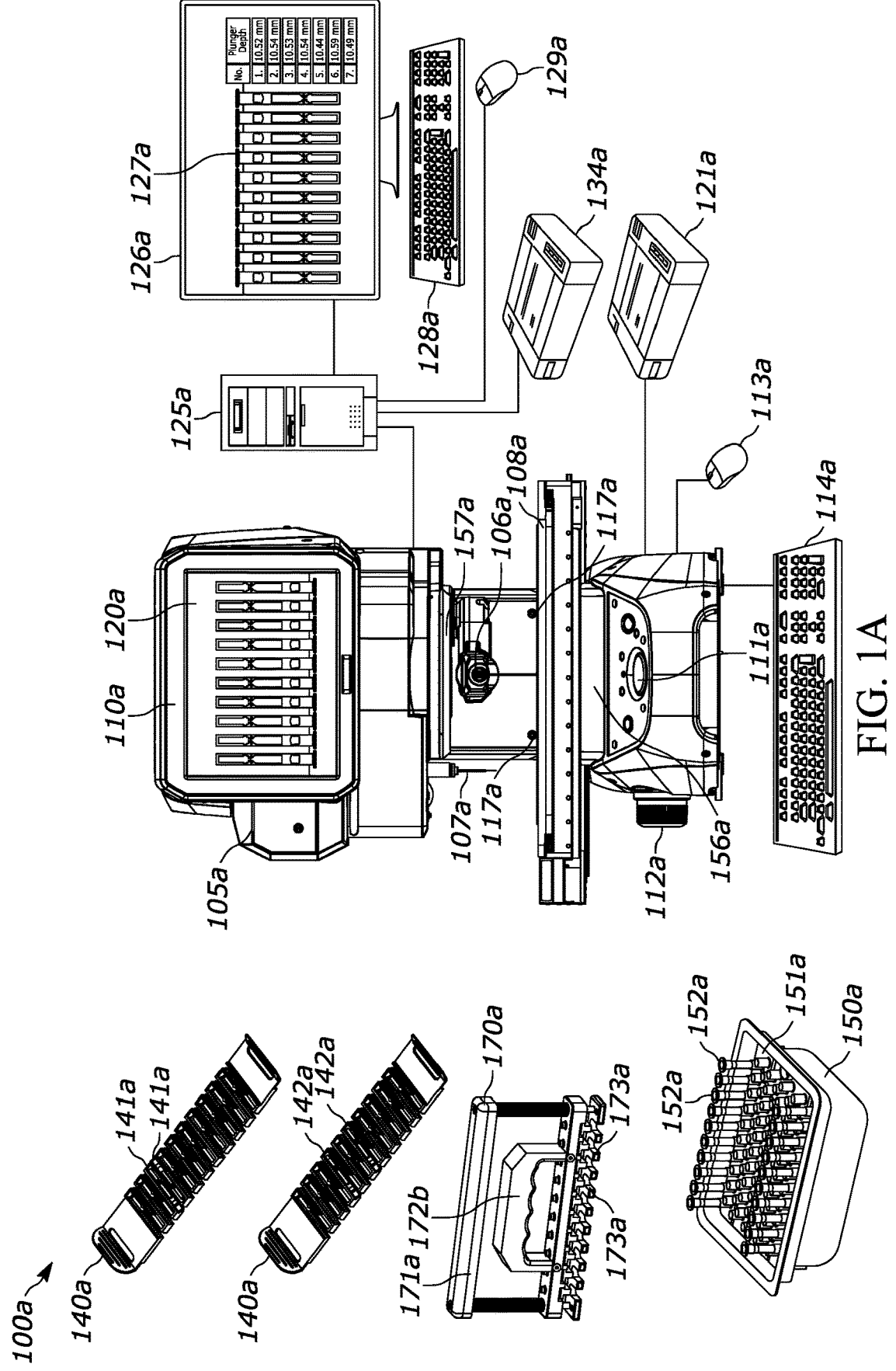
FIG. 1A depicts an example automatic digital image sensor-based syringe plunger depth determination system.

With reference to FIG. 1A, a measurement device 105*a* (e.g., a Keyence IM-7030, available from Keyence Corporation of America, 500 Park Boulevard, Suite 200, Itasca, Il 60143; a PID TRPT-031206 vision system; a DASI vision system; etc.) may be configured to determine a plunger depth within at least one syringe 152*a*, 120*a*, 127*a*. A plurality of syringes 152*a* (e.g., a plurality of pre-filled syringes, a plurality of pre-filled syringe cartridges, etc.) may be transported from, for example, a production process via a tub 150*a* and syringe carrier plate 151*a*. The syringes 152*a* may be removed from the tub 150*a* and the syringe carrier plate 151*a* via, for example, a syringe removal tool 170*a*. The measurement device 105*a* may be calibrated (e.g., trained, etc.) using a rack of syringes 140*a*. The measurement device 105*a* may be communicatively connected to a remote computing device 125*a*.

The measurement device 105*a* may also include a digital camera 106*a* (e.g., a camera including a CMOS or CCD imaging sensor, etc.), a target orientation sensor 107*a*, an imaging surface 108*a* having at least one alignment feature 117*a*, a display device 110*a* having a host of user interface displays 120*a*, a user control panel 111*a*, a manual imaging surface/camera orientation/focus control 112*a*, a mouse 113*a*, a keyboard 114*a*, and a printer 121*a*. The remote device 125*a* may include a display device 126*a* having a plurality of user interfaces 127*a*, a keyboard 128*a*, a mouse 129*a*, and a printer 134*a*. The syringe removal tool 170*a* may include a plurality of syringe receptacles 173*a* and a spring biased syringe retaining portion 171*a*/172*a*. The syringe rack 140*a* may include a plurality of syringes 141*a*, 142*a* secured to the respective syringe rack 140*a* in a pre-determined orientation. Further details of the measurement device 105*a*, the remote device 125*a*, the tub/carrier plate 150*a*, 151*a*, the syringe removal tool 170*a*, and the syringe racks 142*a* are included herein.

Figure 1B:
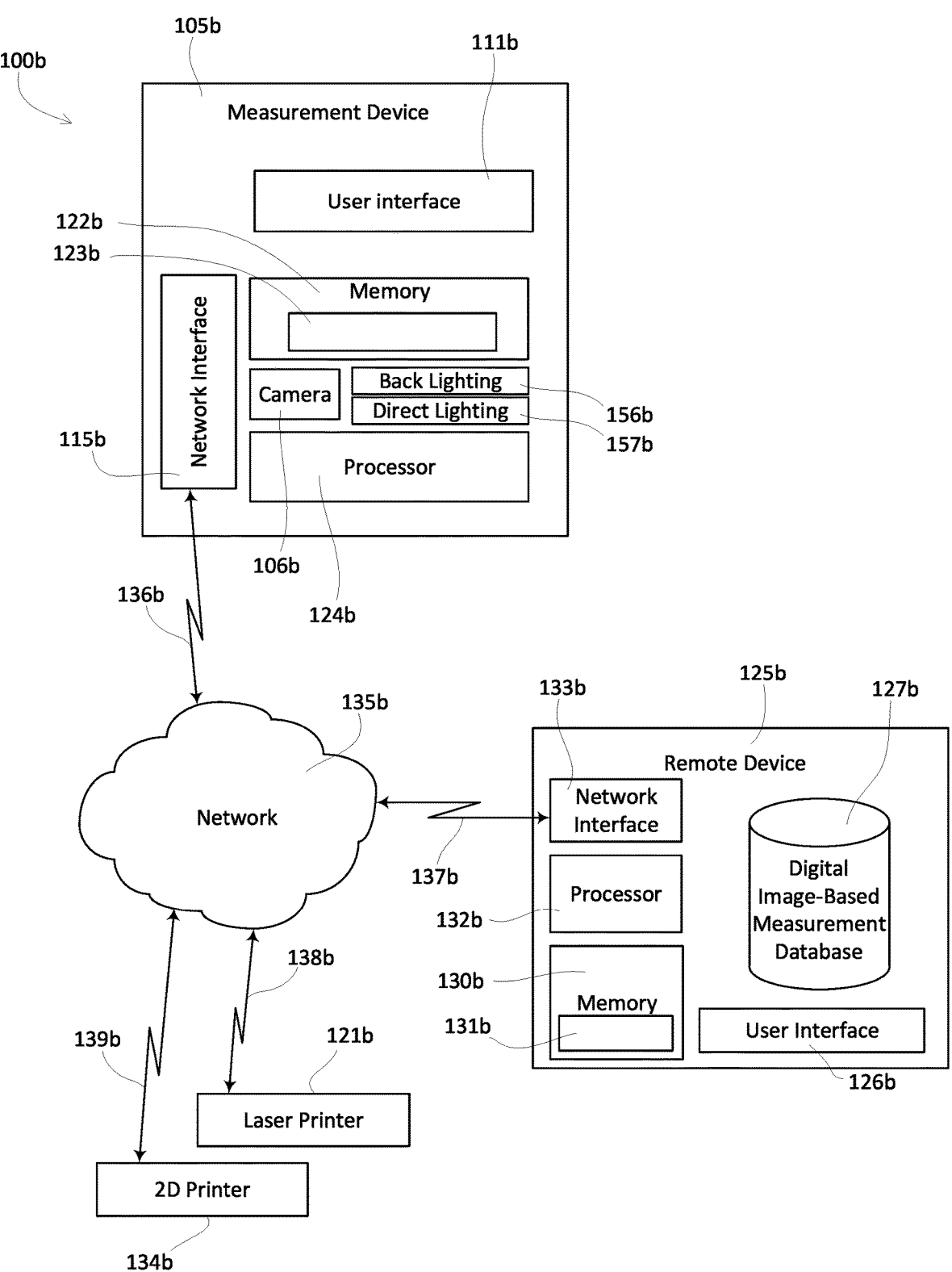
FIG. 1B depicts a high-level block diagram of an example automatic digital image sensor-based syringe plunger depth determination system.

Turning to FIG. 1B, a measurement system 100*b* may include a measurement device 105*b* in communication with a remote device (e.g., a server) 125*b* via a network 135*b*. The measurement device 105*b* may be similar to, for example, the measurement device 105*a* of FIG. 1A. The remote device 125*b* may be similar to, for example, the remote device 125*a* of FIG. 1A.

The system 100*b* may implement communications between the measurement device 105*b* and the remote device 125*b* (e.g., a remote server) to provide, for example, syringe data and/or desired measurement data to a digital image-based measurement database 127*b*.

For example, the system 100*b* may acquire syringe data and/or desired measurement data from, for example, a user of a measurement device 105*b* (e.g., digital image-based measurement device, etc.). Alternatively, or additionally, while not shown in FIG. 1B, syringe data and/or desired measurement data may be automatically obtained from a third party data source (e.g., a syringe manufacture, a medication manufacturer, etc.). As described in detail herein, the system 100*b* may automatically determine a depth of a plunger within at least one syringe, etc.

For clarity, only one measurement device 105*b* is depicted in FIG. 1B. While FIG. 1B depicts only one measurement device 105*b*, it should be understood that any number of measurement devices 105*b* may be supported and that each measurement device 105*b* may be any appropriate digital image-based measurement device. A measurement device 105*b* may include a memory 122*b* and a processor 124*b* for storing and executing, respectively, a module 123*b*. The module 123*b*, stored in the memory 122*b* as a set of computer-readable instructions, may be related to an application for automatically determining a plunger depth within at least one syringe.

As described in detail herein, the module 123*b* may facilitate interaction between an associated measurement device 105*b* and a remote device 125*b*. For example, the processor 124*b*, further executing the module 123*b*, may facilitate communications between a remote device 125*b* and a measurement device 105*b* via a measurement device network interface 115*b*, a measurement device communication link 136*b*, a network 135*b*, a remote device communication link 137*b*, and a remote device network interface 133*b*.

A measurement device 105*b* may include a user interface 111*b* which may be any type of electronic display device, such as touch screen display, a liquid crystal display (LCD), a light emitting diode (LED) display, a plasma display, a cathode ray tube (CRT) display, or any other type of known or suitable electronic display along with a user input device. A user interface 111*b* may exhibit a user interface (e.g., any user interface 120, 127*a*, 120*c*, 127*c*, 120*d*, 127*f*, etc.) which depicts a user interface for configuring a measurement device 105*b* to communicate with a remote device 125*b*.

The network interface 133*b* may be configured to facilitate communications between a measurement device 105*b* and a remote device 125*b* via any wireless communication network 135*b*, including for example a wireless LAN, MAN or WAN, WiFi, the Internet, or any combination thereof. Moreover, a measurement device 105*b* may be communicatively connected to a remote device 125*b* via any suitable communication system, such as via any publicly available or privately owned communication network, including those that use wireless communication structures, such as wireless communication networks, including for example, wireless LANs and WANs, satellite and cellular telephone communication systems, etc. A measurement device 105*b* may cause, for example, projectile and/or stabilizer related data to be transmitted to, and stored in, for example, a remote device 125*b*, memory 130*b*, and/or a remote digital image-based measurement database 127*b*.

A remote device 125*b* may include a user interface 126*b*, a memory 130*b*, and a processor 132*b* for storing and executing, respectively, a module 131*b*. The module 131*b*, stored in the memory 132*b* as a set of computer-readable instructions, may facilitate applications related to automatically determining a plunger depth within at least one syringe. The module 131*b* may also facilitate communications between the remote device 125*b* and a measurement device 105*b* via a network interface 133*b*, and the network 135*b*, and other functions and instructions.

A remote device 125*b* may be communicatively coupled to a digital image-based measurement database 127*b*. While the digital image-based measurement database 127*b* is shown in FIG. 1B as being communicatively coupled to the remote device 125*b*, it should be understood that the digital image-based measurement database 127*b* may be located within separate remote servers (or any other suitable computing devices) communicatively coupled to the remote device 125*b*. Optionally, portions of digital image-based measurement database 127*b* may be associated with memory modules that are separate from one another, such as a memory 122*b* of a measurement device 105*b*.

Figure 1C:
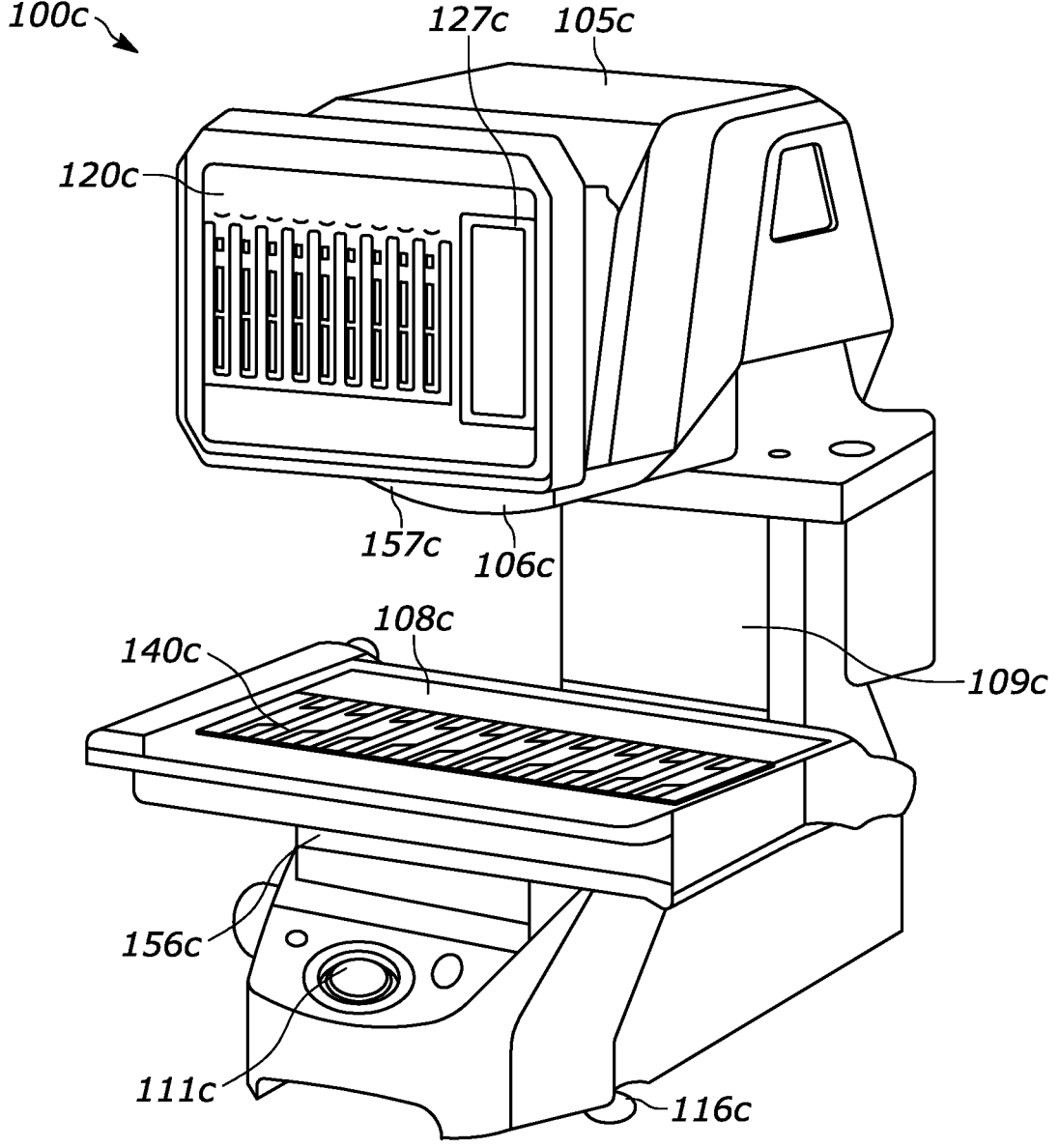
FIGS. 1C-E depict various views of an example automatic digital image sensor-based syringe plunger depth determination device.

With reference to FIG. 1C, an automatic imager 100*c* may include a frame 109*c* and an imaging system. The measurement device 105*c* may be similar to, for example, the measurement device 105*a* of FIG. 1A or the measurement device 105*b* of FIG. 1B. In some examples, the imaging system is movable relative the frame 109*c* or the imaging system may be fixed on the frame 109*c*. Additionally, in the example of FIG. 1C, the automatic imager 105*c* may be designed to be operated on a desktop or workbench. But in some examples, the automatic imager 105*c* may be a larger laboratory apparatus.

The imaging system 100*c* may include a camera 106*c* and illumination source, an imaging surface 108*c* and illumination source. In the example of FIG. 1C, the imaging surface 108*c* may be disposed between the camera 106*c* and an illumination source. As shown, the camera 106*c* may be disposed above the imaging surface 108*c* and an illumination source may be disposed beneath the imaging surface 108*c*. The camera 106*c* and the illumination source can be any known camera and illumination source known in the art.

For example, the camera 106c can be any resolution, mirrored or mirrorless, analog or digital sensors, etc. Additionally, the illumination source can be any known light source including at least one light emitting diode (LED), incandescent bulb, fluorescent, mirrored redirection of light, etc. The imaging surface 108c may be transparent, to allow light from the illumination source to be received by the camera 106c. The imaging surface 108c can be, for example, any plastic, ceramic, glass, or other transparent material.

The imaging system may be disposed on the frame 109c. The frame 109c of the automatic imager 105c may include a base 116c, a head, and a support arm. As shown, the base 116c and the head may be vertically separated. In the present example, the base 116c may include an input system 111c and the head may include a display 110c. However, the input system 111c and the display 110c may be disposed on either the base 116c or the head. Alternatively, the input system 111c and the display 110c may be separate from the frame 109c. For example, the input system 111c may include a keyboard 114a and mouse 113a and the display 110c may include a monitor 126a. In yet further examples, the display 110a and input system 111c may be combined together as a touch-screen display.

As shown, the head may be disposed on the support arm 109c above the base 116c. The support arm 109c may keep the head disposed vertically above the base 116c, but in some examples, the head can be adjustable along the height of the support arm 109c. Accordingly, the head can be either fixed relative the base 116c or movable relative the base 116c. Additionally, in some examples, the head may include a controller or processor (e.g., processor 125b of FIG. 1B), however the processor 124b may be disposed external to the automatic imager 100c. The processor 124b may be configured to receive image data from the camera 106c and also include a communication unit to transmit data to and from a network (e.g., network 135b of FIG. 1B).

In operation, the automated imager 100c may be activated by a user via, for example, user control 111c. When preparing to generate image data, the processor 124b may activate an illumination source disposed on the base 116c and under the imaging surface 108c. A user can then place an object to be imaged, such as a tub 150a of syringes 140a, on the imaging surface 108c. Utilizing the input system 111c, the user can generate image data by taking a picture via the camera 106c. After the image data is generated, the display 110c may present the picture 120c taken via the camera 106c and other measured metrics 127c. In some examples, the picture 120c and the measured metrics 127c, and transmitted to the network 135c via, for example, a network connection 115e after being presented on the display 110c. This secure transmission to the network 135c of the picture and/or the measured metrics can also be transmitted with batch numbers to, for example, track and record syringe manufacturing quality related data. The network 135c could connect to a local data server, a remote data server 125a, or other cloud storage solution.

Figure 1D:
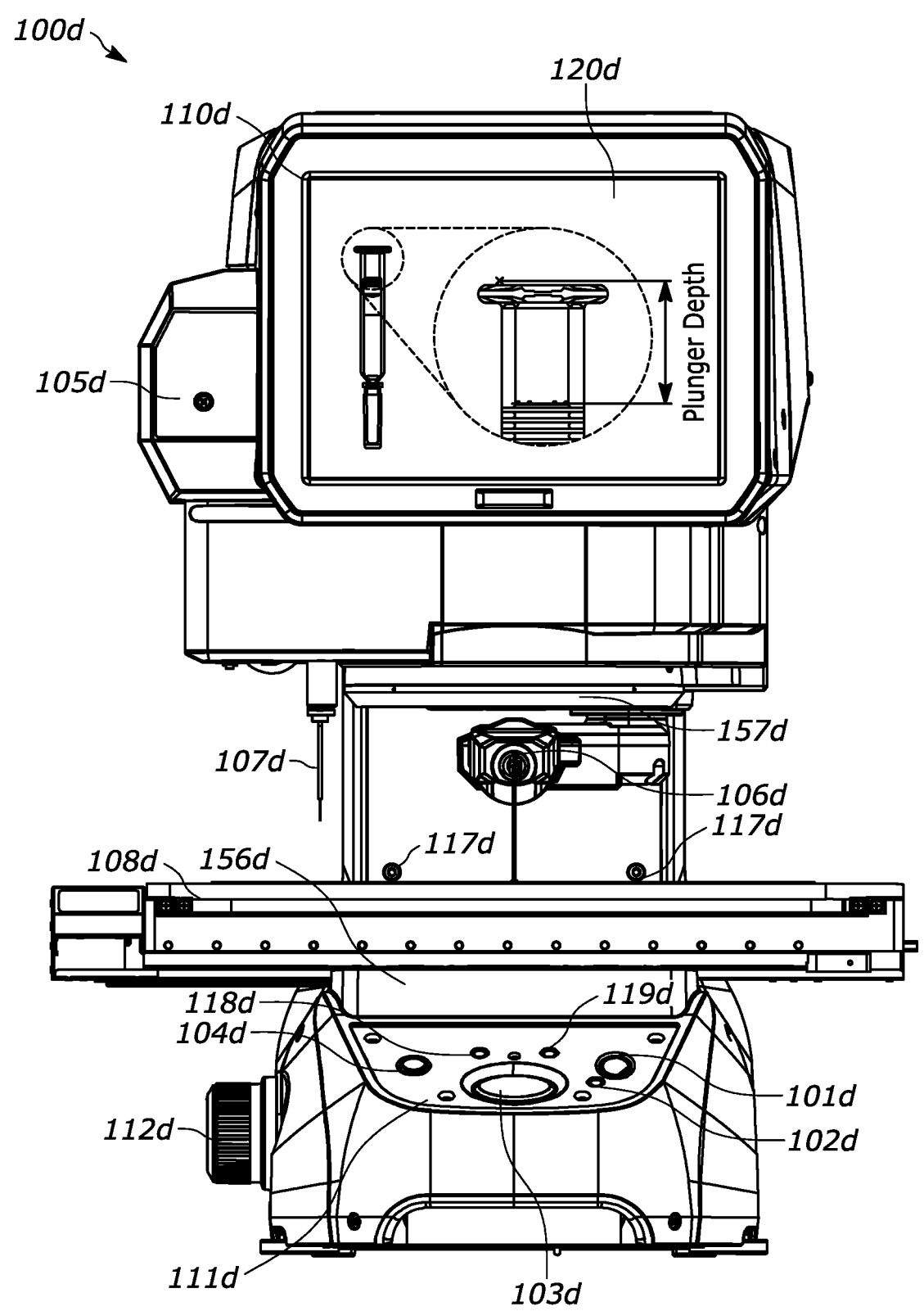
Figure 1E:
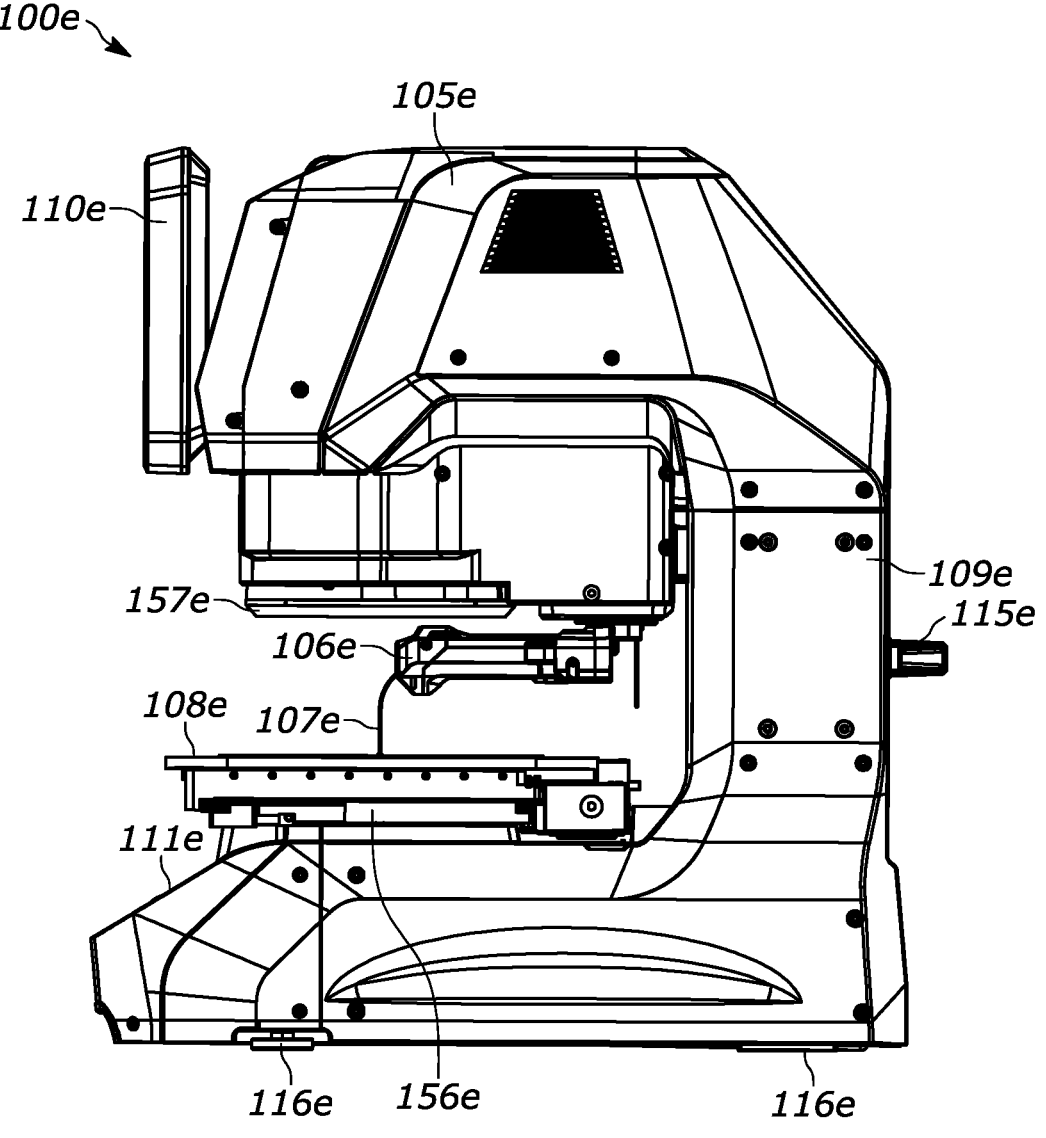

Turning to FIGS. 1D and 1E, a measurement system 100d,e may include a measurement device 105d,e may also include a digital camera 106d,e, a target orientation sensor 107d,e, an imaging surface 108d,e having at least one alignment feature 117d,e, a support structure 109e, a display device 110d,e having a host of user interface displays 120d, a user control panel 111d,e, a manual imaging surface/camera orientation/focus control 112d, a network connection 115e, and a base 116e. The user control panel 111d,e may include a power on button 101d, a power on indicator 102d, a measurement/image orientation control 103d, a print button 104d, a measurement OK indicator 118d, and a measurement NG indicator 119d.

Figure 1F:
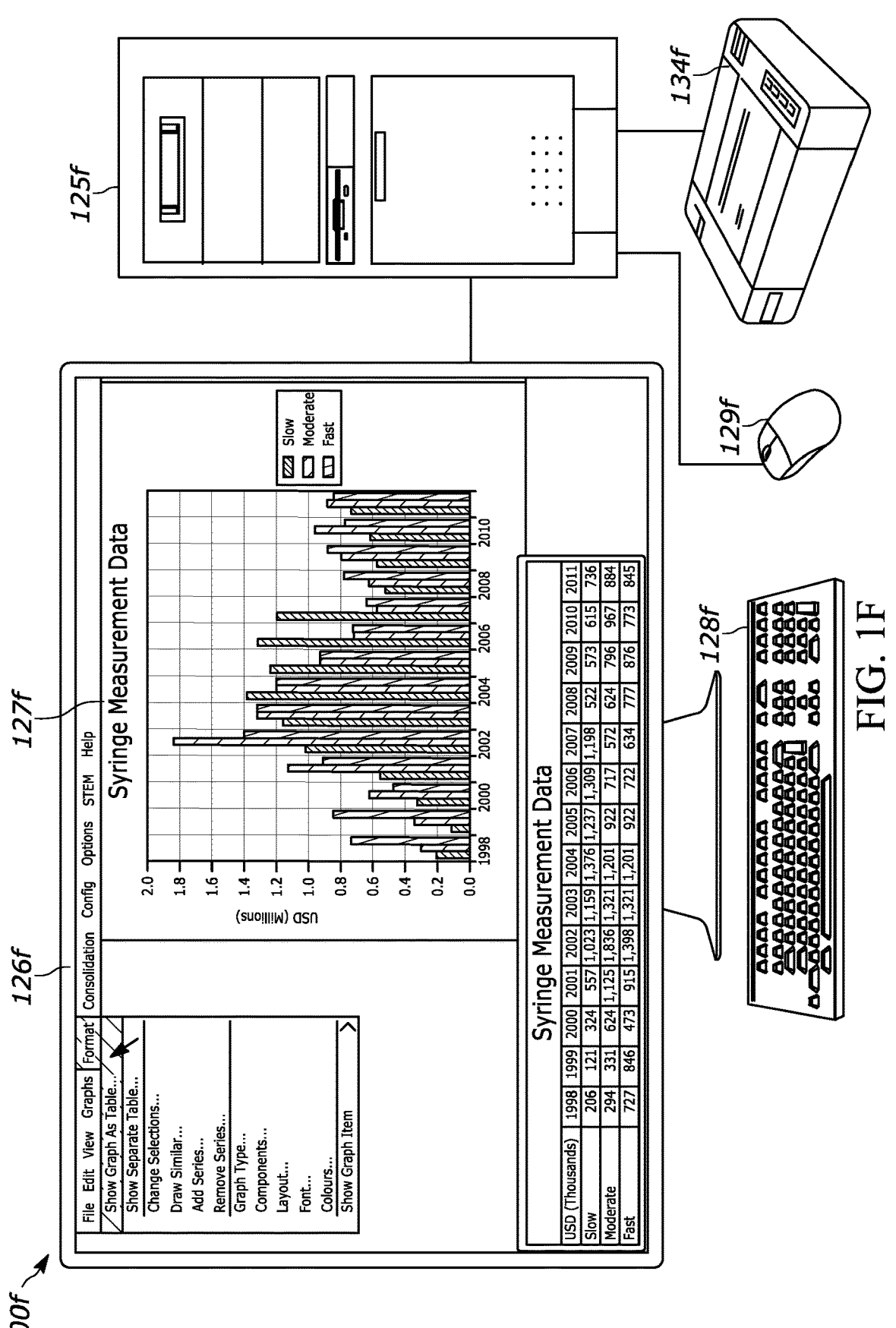
FIG. 1F depicts an example remote computing device for use within an automatic digital image sensor-based syringe plunger depth determination system.

With reference to FIG. 1F, a remote device 125f may include a display device 126f having a plurality of user interfaces 127f, a keyboard 128f, a mouse 129f, and a printer 134f. The measurement device 105a-e may be, for example, configured to automatically determine a plunger depth of a plunger within at least one syringe in response to a user placing at least one syringe 140a onto an imaging surface 108a. Alternatively, or additionally, the measurement device 105a-e may be, for example, configured to automatically determine a plunger depth of a plunger within at least one syringe in response to a user placing at least one syringe 140a onto an imaging surface 108a, and activating a measurement control 103d or print button 104d. More desirably, the measurement device 105a-e may be, for example, configured to automatically determine plunger depths of plungers within a respective syringe of a plurality syringes simultaneously.

While not shown in FIGS. 1A-F, a syringe removal tool 170a may be affixed to (or connectable with), for example, a robotic controlled syringe transfer machine configured to remove a plurality of syringes from a tub, place the plurality of syringes on an imaging surface of a measurement device, and return the plurality of syringes to the tub after the measurement machine has determined a respective plunger depth for each syringe, and electronically recorded/displayed/printed the associated plunger depth measurement results.

Turning to FIG. 2A, a syringe alignment rack assembly 200a may include a syringe rack 241a having a plurality of syringe receptacles 243a, 245a. Each syringe receptacle 243a, 245a may be configured to align a respective syringe 244a, 246a in a pre-determined orientation relative the syringe rack 241a. The syringe rack assembly 200a may also include at least one rack alignment feature 242a configured to align the rack 241a with a syringe plunger depth measurement device 105a. The plurality of syringe receptacles 243a, 245a may be arranged linearly along a length of the rack 241a. The plurality of syringe receptacles 243a, 245a may be configured to retain a plurality of syringes 244a, 246a side-by-side with a needle end of every other of the plurality of syringes 244a, 246a oriented toward a first side of the rack 241a. A needle end of the other of the plurality of syringes 244a, 246a may be oriented toward a second side of the rack 241a. While the syringe alignment rack assembly 200a may be illustrated in FIG. 1A as including twenty syringe receptacles 243a, 245a, the syringe alignment rack assembly 200a may include any number of syringe receptacles 243a, 245a.

The syringe alignment rack assembly 200a may include at least one handle portion 247a. As illustrated, the syringe alignment rack assembly 200a may include a handle portions 247a on each end of the syringe alignment rack assembly 200a. In any event, a handle portion 247a may, for example, extend upward and outward, at an angle from an upper surface of the syringe alignment rack assembly 200a, for easy handling. The syringe alignment rack assembly 200a may further include at least one visual rack alignment marker 248a configured to, for example, provide an alignment reference for a measurement device 105a-e. Alternatively, or additionally, the measurement device 105a-e may be configured to detect an edge of the syringe alignment rack assembly 200a (e.g., an edge of the syringe alignment rack assembly 200a along a first side, an edge of the syringe alignment rack assembly 200a along a second side, etc.).

With reference to FIG. 2B, a syringe alignment rack assembly 200*b* may include a syringe rack 241*b* having a plurality of syringe receptacles 243*b*. Each syringe receptacle 243*b* may be configured to align a respective syringe 244*b* in a pre-determined orientation relative the syringe rack 241*b*. The syringe rack assembly 200*b* may also include at least one rack alignment feature 242*b* configured to align the rack 241*b* with a syringe plunger depth measurement device 105*a*. The plurality of syringe receptacles 243*b* may be arranged linearly along a length of the rack 241*b*. The plurality of syringe receptacles 243*b* may be configured to retain a plurality of syringes 244*b* side-by-side with a needle end of the plurality of syringes 244*b* oriented toward a first side of the rack 241*b*. While the syringe alignment rack assembly 200*b* may be illustrated in FIG. 1B as including eighteen syringe receptacles 243*b* the syringe alignment rack assembly 200*b* may include any number of syringe receptacles 243*b*.

The syringe alignment rack assembly 200*b* may include at least one handle portion 247*a*. As illustrated, the syringe alignment rack assembly 200*b* may include a handle portions 247*b* on each end of the syringe alignment rack assembly 200*b*. In any event, a handle portion 247*b* may, for example, extend upward and outward, at an angle from an upper surface of the syringe alignment rack assembly 200*b*, for easy handling. The syringe alignment rack assembly 200*b* may further include at least one visual rack alignment marker 248*b* configured to, for example, provide an alignment reference for a measurement device 105*a-e*. Alternatively, or additionally, the measurement device 105*a-e* may be configured to detect an edge of the syringe alignment rack assembly 200*b* (e.g., an edge of the syringe alignment rack assembly 200*b* along a first side, an edge of the syringe alignment rack assembly 200*b* along a second side, etc.).

With further reverence to FIG. 2C, a syringe alignment rack 200*c* may be similar to either a portion of the syringe alignment rack 200*a* or a portion of the syringe alignment rack 200*b*. In any event, the syringe receptacles 243*a*, 245*a*, 243*b* may include an open end 245*c* that may, for example, define a syringe barrel receptacle 243*c* configured to receive a syringe barrel 252*c*. A bottom surface (e.g., bottom surface 814 of FIGS. 4B and 4C) of a flange end 246*c* of a syringe 244*c* may rest against a perimeter of the open end 245*c* (i.e., similar to a relationship of the bottom surface 814 with a respective syringe receptacle 473*c* as illustrated in FIG. 4C). The syringe receptacles 243*a*, 245*a*, 243*b* may also include syringe registration tabs 248*c* that may be, for example, configured to engage a distal end 249*e* of a respective syringe barrel 252*c*.

The syringe receptacles 243*a*, 245*a*, 243*b* may further include a closed end that may, for example, define a capped needle receptacle 250*c* configured to receive a capped needle end 251*c* of the syringe 244*c*. As illustrated, the capped needle receptacle 250*c* may be, for example shorter than the barrel receptacle 243*c* (e.g., a length of the barrel receptacle 243*c* may based on a length of a respective syringe barrel 252*c*, a length of the capped needle receptacle 250*c* may be based on a length of a respective capped needle end 251*c*, etc.).

The syringe barrel receptacle 243*c* may include curved side surfaces 247*c* that may, for example, conform to a portion of a perimeter surface of an associated syringe barrel 244*c*. As illustrated, a portion of the barrel receptacle between the curved side surfaces 247*c* may be open, such that, for example, a camera (e.g., camera 105*a-e* of FIGS. 1A-1E) of a measurement device 105*a-e* may image at least a portion of a length of a syringe barrel 252*c* and plunger 253*c* that is back lit via an back light source (e.g., back light source 156*a* of FIG. 1A).

A syringe rack assembly 200*a-c* may be, at least partially made of plastic, rubber, etc. In at least one embodiment, the syringe rack assembly 200*a-c* is made of materials that do not result in any metal to glass contact between the syringe rack assembly 200*a-c* and respective syringes and/or cartridges. A pre-determined measurement tolerance (e.g., a measurement accuracy tolerance associated with a plunger depth measurement with respect to a syringe) may be, for example, a sum of a syringe-to-rack registration tolerance, a rack-to-imaging device registration tolerance, and a measurement device (e.g., measurement device 105*a-e* of FIGS. 1A-E) tolerance. In at least one embodiment, the sum of the syringe-to-rack registration tolerance, the rack-to-imaging device registration tolerance, and the measurement device 105*a-e* tolerance is less than the pre-determined measurement tolerance.

Turning to FIGS. 3A and 3B, a syringe transport assembly 300*a,b* may include a tub 350*a* configured to receive a plurality of syringes 352*a*. The syringe transport assembly 300*a,b* may also include a syringe carrier plate 351*a* have a plurality of apertures extending from a top surface of the syringe carrier plate to a bottom surface of the syringe carrier plate. Each of the plurality of syringes 352*a* may be, for example, linearly inserted into a respective one of the plurality of apertures. The syringe transport assembly 300*a,b* may further include a tub insert 353*b* configured to be placed within the tub 350*a* prior to the plurality of syringes 352*a* being placed into the tub 350*a*, wherein the tub insert 353*b* may include at least one syringe elevator 355*b* linearly aligned with at least one of the plurality of syringes 352*a*. When the syringe carrier plate 351*a* and the plurality of syringes 352*a* are placed within the tub 350*a*, the at least one syringe that is linearly aligned with the at least one syringe elevator 355*b* may be linearly elevated relative to the remaining syringes of the plurality of syringes 352*a*.

The plurality of apertures in the syringe carrier plate 351*a* may be arranged in a plurality of rows and a plurality of columns. The tub insert 353*b* may include two syringe elevators 355*b*. A first one of the syringe elevators may be aligned with a first row of the plurality of apertures. A second one of the syringe elevators 355*b* may be aligned with a second row of the plurality of apertures. The tub insert 353*b* may include an upper lip 354*b* configured to align the syringe carrier plate 351*a* relative the tub 350*a* when a perimeter of the syringe carrier plate 351*a* is received within the upper lip 354*b*. While the syringe transport assembly 300*a,b* may be illustrated in FIGS. 3A and 3B as including an array of ten-by-ten syringes 352*a*, the syringe transport assembly 300*a,b* may include any number of syringes 352*a*. In at least one embodiment, a number of syringes 352*a* aligned with a syringe elevator 355*b* is equal to, or less than, a number of syringe receptacles (e.g., syringe receptacles 473*a* of FIG. 4A) of an associated syringe removal tool (e.g., syringe removal tool 470*a* of FIG. 4A).

Turning to FIG. 4A, a syringe removal tool 470*a* may include a syringe carrier 477*a* having a first end, a second end, and a plurality of syringe receptacles 473*a* linearly arranged along an edge of the syringe carrier 477*a* that extends from the first end to the second end. While the syringe removal tool may be illustrated in FIG. 4A as including ten syringe receptacles 473*a*, the syringe removal tool may include any number of syringes receptacles 473*a*. In at least one embodiment, a number of syringe receptacles 473*a* is equal to, or greater than, a number of associated syringes (e.g., syringes 352a of FIG. 3A) aligned with a syringe elevator (e.g., syringe elevator 355b of FIG. 3B).

The syringe removal tool 470a may be configured to remove a plurality of syringes 152a from a tub 150a. The syringe removal tool 470a may also include a stationary grip portion 471a having a first end and a send end. The first end of the syringe carrier 477a may be connected to the first end of the stationary grip portion 471a via a first slide rod 476a. The second end of the syringe carrier 471a may be connected to the second end of the stationary grip portion 471a via a second slide rod 476a. The syringe retainer portion 475a may include a first end, a second end, and a plurality of spring biased syringe retainers 478a/479a linearly arranged along the syringe retainer portion 475a from the first end to the second end. Each spring biased syringe retainer 478a may be configured to retain a respective syringe within a respective syringe receptacle 473a independent of any other spring biased syringe retainer 478a in the plurality of spring biased syringe retainers 478a. The first end of the syringe retainer portion 475a may be configured to slide along the first slide rod 476a. The first end of the syringe retainer portion 475a may be biased toward the first end of the syringe carrier portion 477a via a first syringe retainer portion bias spring 474a. The second end of the syringe retainer portion 475a may be configured to slide along the second slide rod 476a. The second end of the syringe retainer portion 475a may be biased toward the second end of the syringe carrier portion 477a via a second syringe retainer portion bias spring 474a. The syringe carrier portion 477a and the plurality of syringe retainers 478a may be, at least partially made of plastic, rubber, etc. In at least one embodiment, the syringe carrier portion 477a and the plurality of syringe retainers 478a may include non-metallic surfaces (e.g., plastic surfaces, rubber surfaces, nylon surfaces, etc.) that contact with each of a plurality of syringes (e.g., glass surfaces, etc.).

The tool 470a may also include at least one tool alignment feature 471a1, 471a2. configured to align the tool 470a with a syringe plunger depth measurement device 105a (e.g., tool alignment features 471a1 may engage with an alignment feature 117a, or alignment feature 582a of FIG. 5A). A pre-determined measurement tolerance (e.g., a measurement accuracy tolerance associated with a plunger depth measurement with respect to a syringe) may be, for example, a sum of a syringe-to-syringe removal tool registration tolerance, a syringe removal tool-to-imaging device registration tolerance, and a measurement device (e.g., measurement device 105a-e of FIGS. 1A-E) tolerance. In at least one embodiment, the sum of the syringe-to-syringe removal tool registration tolerance, the syringe removal tool-to-imaging device registration tolerance, and the measurement device 105a-e tolerance is less than the pre-determined measurement tolerance.

With reference to FIG. 4B, a measurement system 400b is illustrated to include a section of a syringe retainer portion 475b (e.g., a section of a syringe retainer portion 475a of FIG. 4A) in proximity with a syringe (e.g., a syringe 802 of FIG. 7E). As described with regard to FIG. 4A, the syringe retain portion 475a,b may include a first end, a second end, and a plurality of spring biased syringe retainers 478a/479a linearly arranged along the syringe retainer portion 475a from the first end to the second end. Each spring biased syringe retainer 478a may be configured to retain a respective syringe within a respective syringe receptacle 473a independent of any other spring biased syringe retainer 478a in the plurality of spring biased syringe retainers 478a. The first end of the syringe retainer portion 475a may be configured to slide along the first slide rod 476a. The first end of the syringe retainer portion 475a may be biased toward the first end of the syringe carrier portion 477a via a first syringe retainer portion bias spring 474a. The second end of the syringe retainer portion 475a may be configured to slide along the second slide rod 476a. The second end of the syringe retainer portion 475a may be biased toward the second end of the syringe carrier portion 477a via a second syringe retainer portion bias spring 474a. The syringe carrier portion 477a and the plurality of syringe retainers 478a may be, at least partially made of plastic, rubber, etc. In at least one embodiment, the syringe carrier portion 477a and the plurality of syringe retainers 478a may include non-metalic surfaces (e.g., plastic surfaces, rubber surfaces, nylon surfaces, etc.) that contact with each of a plurality of syringes (e.g., glass surfaces, etc.).

As further illustrated in FIG. 4B (similar to FIG. 7E), a syringe 404 may include a needle cap 310 covering a needle (not seen), a syringe barrel 312, a plunger 314, a medicament 316, a bubble 318, and a flange 810. The syringe barrel 312 may be transparent or translucent. Conventionally, the needle may be coupled to the syringe barrel 312 at a needle hub. The needle hub can include, for example, a syringe shoulder formed integrally with the barrel 312 and coupled directly to the needle (forming what is commonly referred to as a "staked needle"), a Luer lock style connector, and/or any other mechanism for directly or indirectly coupling the syringe with the needle. The flange 810 is disposed on the distal end of the syringe 802, opposite the needle and needle cap 310. The flange 810 includes a proximal end 814 and a distal end 812. Similarly, as shown in FIG. 7E, the plunger 314 may also include a proximal end 822 and a distal end 820, the distal end 820 being closest to the flange 810. The flange 810 may include a lower surface 814.

Turning to FIG. 4C, a measurement system 400c may include a syringe receptacle 473c (e.g., similar to a portion of syringe receptacle 473b of FIG. 4B), a spring biased syringe retainer 478c (e.g., similar to a portion of a spring biased syringe retainer 478b/479b of FIG. 4B), syringe retain portion 475c (e.g., similar to a portion of syringe retain portion 475a,b of FIGS. 4A and 4B), and a section of a syringe (e.g., a section of a syringe 404 of FIGS. 4B and 7E). In any event, a lower surface 810 of the syringe flange 810 may be biased toward an upper surface of a syringe receptacle 473c via, for example, a respective spring biased syringe retainer 478c. The spring biased syringe retainer may include a syringe flange contact 478c, a slide rod 479c3, a bias spring 479c2, and a fastener 479c1. The bias spring 479c2 may be configured to bias the syringe flange contact 478c toward the upper surface of the syringe receptacle 473c, thereby, securing the syringe 404 to the syringe receptacle 473c. The slide rod 479c3 may correspondingly slide within the aperture 475c1 to the syringe retain portion 475c. A lower surface of the spring biased syringe retainer 478c may include a non-metal surface (e.g., a plastic surface, a nylon surface, a rubber surface, etc.).

With reference to FIG. 4D, a measurement system 400d may include a syringe removal tool 202 in operable relationship with a tub 204 of syringes. For quality control, a tub 204 containing a multiplicity of syringes 210 may be provided for evaluation. In some examples, each syringe of the multiplicity of syringes 210 in the tub 204 needs to be evaluated. In other examples, only a subset of the multiplicity of syringes 210 needs to be evaluated. For example, a user may only need to take one row of syringes 212a or fill a single of syringes 212b. In total, the tub 204 may contain over 160 syringes.

Turning to FIGS. 4E-F, a measurement system 400*e*-*f* and method may include a user (e.g., a lab technician, a syringe manufacturer, etc.) handling a plurality of syringes 300 in accordance with the present disclosure. As shown, each of the plurality of syringes 300 includes a needle disposed in a needle cap 310, a syringe barrel 312, a plunger 314, medicament 316, and a bubble 318. In accordance with the present disclosure, a person (e.g., a lab technician, a manufacture,) may shake 330 the plurality of syringes 300 to cause the bubble 318 in each syringe to move in the syringe barrel 312 approximate the needle and needle cap 310.

As shown in FIG. 4E, a measurement system 400*e* may include a syringe 402 having a bubble 318 proximate a needle and needle cap 310. In contrast, the bubble 318 in a syringe 404 may be disposed approximate the plunger 314. After the shake 330 and as shown in FIG. 4F, a measurement system 400*f* may detect a bubble 318 in each syringe 402 and 404 that is disposed approximate the needle cap 310 and the medicament 316 is disposed approximate the plunger 314.

With reference to FIG. 5, a syringe and measurement device alignment assembly 500 may include an alignment adapter 580. The alignment adapter 580 may include at least one measurement device alignment feature 581 configured to, for example, engage with an alignment feature (e.g., alignment feature 117*a* of FIG. 1A) of a measurement device 105*a*. The alignment adapter 580 may also include at least one syringe rack alignment feature 582 configured to, for example, engage with an alignment feature (e.g., alignment feature 242*a,b* of FIGS. 2A and 2B, respectively) of a syringe rack 241*a,b*. The syringe and measurement device alignment assembly 500 may be, for example, configured to align a syringe rack 241*a,b* or a syringe removal tool (e.g., syringe removal tool 170*a* of FIG. 1A) with a camera (e.g., camera 106*a* of FIG. 1A) in a pre-determined orientation relative one another.

Turning to FIGS. 6A and 6B, a plurality of syringes 300 are being placed on an imaging surface 108*c* of the automatic imager 100*c* of FIG. 1C. As shown in FIGS. 6A and 6B, the imaging surface 108*c* includes a front edge 612, a back edge 614, and side edges 616. The plurality of syringes 300 (e.g., syringes similar to, for example, syringes 152*a* of FIG. 1A) may be placed generally centrally on imaging surface 114 (e.g., imaging surface similar to, for example, imaging surface 108*a* of FIG. 1A), but the plurality of syringes 300 can be disposed anywhere on the imaging surface 114 also in view of the camera 110 (e.g., a camera similar to camera 106*a* of FIG. 1A). As shown, the plurality of syringes 300 are disposed in a single row, parallel with the imaging surface 114 and the front edge 612. In some examples, the plurality of syringes can be arranged in a syringe storage that is aligned, relative the imaging surface 114, with the assistance of an alignment mechanism 630. The alignment feature 630 can be secured to the frame 102 via fasteners 710*a* and 710*b*, may be integrally formed with the imaging surface 114 or the base 122, or coupled to the imaging system 104 by any other known method.

With reference to FIG. 7A, a side view of syringe alignment is illustrated relative a camera 110. In some examples, the imaging system 104 may be sensitive to a rotation angle 1210 of the syringe barrel 312 relative the camera 110. For example, the syringe barrel 312 may include a planar portion 1220 that affects the light passing through the syringe barrel 312 and then captured by the camera 110. In such examples, it may be preferable for the planar portion 1220 to be disposed perpendicular to the camera 110. In the example of FIG. 7A, the planar portion 1220 is perpendicular to the camera when the syringe barrel 312 is at 0, 180, or 360 degrees (°). As shown in FIG. 7A, the syringe 1232*a* is perpendicular to the camera and is at 0° or 360° while the syringe 1232*b* is shown at 45°.

Accordingly, if the camera 110 is sensitive to the angle of the syringe barrel 312, the camera 110 may only be able to get an accurate picture of the syringe 1232*a*. Accordingly, in some examples, when the plurality of syringe 300 is placed on the imaging surface 114, each of the syringes 300 may need to be rotated to be aligned with the camera 110. However, some cameras 110 and imaging systems 104 can take accurate pictures regardless of the angle of the syringe 1232*a* and 1232*b*.

Turning to FIG. 7B, an example display 130 (e.g., a display similar to display 110*a* of FIG. 1A) is illustrated presenting the picture 142 of plunger depth measured metrics 144 of the plurality of syringes 300. As shown in the example display 130, the first syringe 902 has a plunger depth measurement 910 of 10.52 millimeters (mm). The plunger depth measurement is shown in the measured metrics 144 in the first row 912. Accordingly, each syringe of the plurality of syringes shown in the picture 142 corresponds to a row in the measured metrics 144 presented on the example display 130.

In accordance with the present disclosure, the processor 132 processes the picture 142 and measures the plunger depth 910. Because the distance between the camera 110 and the imaging surface 114 is known, the processor can accurately measure a distance in the image. Additionally, the processor 132 can measure the plunger depth 910 of each syringe in the picture 142 rapidly. In some examples, after the processor 132 measure the plunger depth 910 relative the distal end of the syringe, the processor 132 verifies the plunger depth 910 is correct (e.g., within a predetermined tolerance) for the given drug product.

With reference to FIG. 7C, an example display of a first syringe 1002 is illustrated as having a correct plunger depth measurement 1006 and a second syringe 1012 having an incorrect plunger depth measurement 1016. As shown, the plunger depth measurement 1006 was based on the correct identification of the distal end 820 of the plunger 314. As a result, the plunger depth measurement 1006 correctly measures the distance from the distal end of the flange (not shown) to the distal end 820 of the plunger 314. In contrast, the plunger depth measurement 1016 incorrectly measures the distance between the proximal end of the flange (not shown) with an edge of the bubble 318.

With reference to FIG. 7D, an example method 1100 of syringe plunger insertion and equilibration is illustrated. In the first step 1102, the syringe is filled with medicament 316. At a second step 1110, the syringe barrel 312 and the medicament 316 are exposed reduced pressure 1112. In some examples, the reduced pressure 1112 may be vacuum or near vacuum conditions. As a result, at the end of the second step 1110, a portion 1114 of the syringe barrel 312 is exposed to reduced air pressure.

At a third step 1120, a rod 1122 inserts the plunger 314 into the barrel 312 of the syringe. The plunger 314 is inserted into the barrel 312 while the barrel 312 is still exposed to reduced pressure 1112 conditions, and possibly vacuum or near vacuum pressures. While the plunger 314 is inserted, the syringe barrel may include a cavity 1114 that is repressurized due to liquid evaporation in the reduced pressure 1112.

At a fourth step 1130, the syringe barrel 312 is again exposed to normal atmospheric conditions 1132. Such conditions may cause the plunger 314 to move further into the syringe barrel 312. The plunger 314 may continue to be pushed further into the syringe barrel 312 until a fifth step 1140, at which point the pressures 1142 about the plunger 314 are finally equalized. As shown at the fifth step 1140, the pressures 1142 on either side of the plunger 314 is approximately atmospheric pressure. But in some examples, friction forces may cause a small pressure differential between the cavity 1114 and atmospheric pressure. The syringe can then, in a final sixth step 1150, be returned to a tub for later inspection.

Turning to FIG. 7E, a side view of a plunger depth measurement 800. As shown, the example syringe 802, substantially identical to syringe 402 and syringe 404, includes the needle and needle cap 310, the syringe barrel 312, the plunger 314, the medicament 316, the bubble 318, and the flange 810. The flange 810 is disposed on the distal end of the syringe 802, opposite the needle and needle cap 310. The flange 810 includes a proximal end 814 and a distal end 812. Similarly, as shown in FIG. 7E, the plunger 314 also includes a proximal end 822 and a distal end 820, the distal end 820 being closest to the flange 810.

In accordance with the present disclosure, the plunger depth measurement 800 is measured as the distance between the distal end 812 of the flange 810 to the distal end 820 of the plunger 314. The measurement 800 excludes any nubs 824 or irregular protuberances created during the manufacturing process and disposed on the distal end 820 of the plunger 314. The plunger depth measurement 800 is unique to each drug product, container, and fill volume. As a result, the plunger depth measurement 800 is useful in verifying quality of the manufactured product.

With reference to FIG. 8A, a measure device 805a may include a user interface generation module 881a, a syringe data receiving module 882a, a desired measurement data receiving module 883a, an image data receiving module 884a, a manual image orientation/focus data receiving module 885a, a plunger location data determination module 887a, a measurement input receiving module 886a, a print measurement input receiving module 888a, and a measurement data transmission module 889a, for example, stored on a memory 822a as a set of computer-readable instructions. In any event, the modules 881a-889a may be similar to, for example, the module 123b of FIG. 1B.

Turning to FIG. 8B, a method of operating a measurement device 800b may be implemented by a first processor (e.g., processor 124b of measure device 105b of FIG. 1B) executing, for example, at least a portion of modules 881a-889a of FIG. 8A, and/or a second processor (e.g., processor 132b of remote device 125b of FIG. 1B) executing, for example, at least a portion of modules 991b-996b of FIG. 1B. In particular, processor 124b may execute the user interface generation module 881a to cause the processor 124b to, for example, generate a user interface 120a, 127a, 120c, 127c, 120d, 127f (block 881b).

Processor 124b may execute the syringe data receiving module 882a to cause the processor 124b to, for example, (block 882b). Processor 124b may execute the desired measurement data receiving module 883a to cause the processor 124b to, for example, receive desire measurement data from a remote device (block 883b). Processor 124b may execute the image data receiving module 884a to cause the processor 124b to, for example, receive image data (e.g., real-time image data) from a camera 106a (block 884b). Processor 124b may execute the manual image orientation/focus data receiving module 885a to cause the processor 124b to, for example, receive manual image orientation/focus data from a user via a user input device 111a, 112a (block 885b). Processor 124b may execute the measurement input receiving module 886a to cause the processor 124b to, for example, receive a measurement input from a user via a user input 111a (block 886b).

Processor 124b may execute the plunger location data determination module 887a to cause the processor 124b to, for example, determine plunger location data based on digital image data (block 887b). Processor 124b may execute the print measurement input receiving module 888a to cause the processor 124b to, for example, receive a print measurement input from a user via a user interface 111a (block 888b). Processor 124b may execute the a measurement data transmission module 889a to cause the processor 124b to, for example, transmit measurement data to a remote device (block 889b).

With reference to FIG. 9A, a remote device 925a may include a user interface generation module 991a, a syringe data receiving module 992a, a desired measurement data receiving module 993a, a desired measurement data transmission module 994a, a measurement data receiving module 995a, and a measurement data analysis module 996a, for example, stored on a memory 930a as a set of computer-readable instructions. In any event, the modules 1810d-1830d may be similar to, for example, the module 1898a of FIG. 18A.

Turning to FIG. 9B, a method of operating a measurement device 800b may be implemented by a first processor (e.g., processor 124b of measure device 105b of FIG. 1B) executing, for example, at least a portion of modules 881a-889a of FIG. 8A, and/or a second processor (e.g., processor 132b of remote device 125b of FIG. 1B) executing, for example, at least a portion of modules 991b-996b of FIG. 1B. In particular, processor 132b may execute the user interface generation module 991a to cause the processor 132b to, for example, generate a user interface 120a, 127b, 120c, 127c, 120d, 127f, etc. (block 991b).

Processor 132b may execute the syringe data receiving module 992a to cause the processor 132b to, for example, receive syringe data from a user via a user interface (block 992b). Processor 132b may execute the desired measurement data receiving module 993a to cause the processor 132b to, for example, receive desired measurement data from a user via a user interface (block 993b).

Processor 132b may execute the desired measurement data transmission module 994a to cause the processor 132b to, for example, transmit desired measurement data to a measurement device (block 994b). Processor 132b may execute the measurement data receiving module 995a to cause the processor 132b to, for example, receive measurement data from a measurement device (block 995b). Processor 132b may execute the measurement data analysis module 996a to cause the processor 132b to, for example, analyze measurement data (block 996b).

The above description describes various devices, assemblies, components, subsystems and methods for use related to a drug delivery device such as a pre-filled syringe. The devices, assemblies, components, subsystems, methods or drug delivery devices (i.e., prefilled syringe) can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir within the pre-filled syringe for example. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgrastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-$\alpha 4\beta 7$ mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL 15 antibody, see U.S. Pat. No. 7,153,507); Tysabri® (natalizumab, anti-α4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type| receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL 12 mAb (ABT-874); anti-IL12/IL23 mAb (CNTO 1275); anti-IL 13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCI for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRAS$^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BITER (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BITE® (bispecific T cell engager) molecule. In some embodiments, the drug delivery device may contain or be used with AMG 673 or another product containing a half-life extended (HLE) anti-CD33× anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A method of rapid syringe quality verification, comprising:

providing an imaging system including an imaging surface and a processor;

securing a syringe in an alignment device, the alignment device comprising:

(a) a syringe rack defining a syringe receptacle receiving and aligning the syringe relative to the syringe rack, the syringe receptacle comprising an open end with a perimeter against which a flange end of the syringe rests, or (b) a spring actuated mechanism retaining the syringe;

aligning the syringe on the imaging surface relative to the imaging system by disposing the alignment device on the imaging surface, the syringe having a transparent or translucent syringe barrel including a distal end and a proximal end, and a plunger disposed inside of the syringe barrel and located at a plunger depth relative to the distal end of the syringe barrel;

capturing an image of the syringe, including the plunger and a distal end of the syringe;

measuring, via the processor, the plunger depth; and determining, via the processor, whether the plunger depth is within a predetermined tolerance.

2. The method of rapid syringe quality verification of claim 1, wherein:

the imaging system comprises a digital optical comparator; and/or the image comprises an illuminated silhouette.

3. The method of rapid syringe quality verification of claim 1, wherein:

(a) the flange end is disposed on a distal end of the syringe; or (b) the flange end is disposed on a distal end of the syringe;

the plunger includes a distal end and a proximal end opposite the distal end;

the flange end includes a distal end and a proximal end opposite the distal end; and the plunger depth is measured as a distance between the distal end of the flange and the distal end of the plunger.

4. The method of rapid syringe quality verification of claim 1, further including:

aligning a planar portion of the syringe barrel relative to the imaging system; and/or generating syringe quality data and storing syringe quality data.

5. A method of analyzing a plurality of syringes, comprising:

providing an alignment device, carrying a plurality of syringes, each syringe including a transparent or translucent syringe barrel having a distal end and a proximal end, a flange end at the distal end, and a plunger disposed inside of the syringe barrel, the alignment device comprising:

(a) a syringe rack defining a plurality of syringe receptacles receiving and aligning the plurality of syringes relative to the syringe rack, each of the plurality of syringe receptacles comprising an open end with a perimeter against which the flange end of a syringe of the plurality of syringes rests, or (b) a spring actuated mechanism retaining the plurality of syringes;

providing an imaging system, including an imaging surface having at least one alignment tab;

disposing the alignment device and the plurality of syringes on the imaging surface against the at least one alignment tab;

capturing an image, via a camera, of the alignment device and the plurality of syringes; and measuring, via a processor, a plunger depth relative to the distal end of the syringe barrel of each plunger disposed in each of the plurality of syringes; and determining, via the processor, whether the plunger depth of each plunger is within a predetermined tolerance.

6. The method of analyzing a plurality of syringes of claim 5, wherein:

the imaging system comprises a digital optical comparator; and/or the image comprises an illuminated silhouette of each syringe.

7. The method of analyzing a plurality of syringes of claim 5, wherein:

(a) each plunger includes a distal end and a proximal end opposite the distal end; or (b) each plunger includes a distal end and a proximal end opposite the distal end;

each flange end includes a distal end and a proximal end opposite the distal end; and each plunger depth is measured as a distance between the distal end of the respective flange end and the distal end of the respective plunger.

8. The method of analyzing a plurality of syringes of claim 5, further including:

aligning a planar portion of each syringe barrel relative to the imaging system; and/or generating syringe quality data and storing syringe quality data.

9. An automatic syringe measurement system, comprising:

an imaging system capable of generating imaging data, including a camera, an imaging surface, and an illumination source;

an alignment device for aligning at least one syringe relative to the imaging system, the alignment device comprising:

(a) a syringe rack defining at least one syringe receptacle receiving and aligning the at least syringe relative to the syringe rack, the at least syringe receptacle comprising an open end with a perimeter against which a flange end of the at least one syringe rests, or (b) a spring actuated mechanism retaining the at least one syringe; and a processor configured to receive the imaging data from the imaging system to determine whether a depth of a plunger within a barrel of the at least one syringe is within a predetermined tolerance.

10. The automatic syringe measurement system of claim 9, further comprising an alignment tab disposed on the imaging surface and configured to align the alignment device relative to the imaging system.

11. The automatic syringe measurement system of claim 9, wherein:

the imaging system comprises a digital optical comparator; and/or the imaging data generated by the imaging system includes illuminated silhouette image of the at least one syringe.

12. The automatic syringe measurement system of claim 9, wherein the imaging surface is disposed between the camera and the illumination source.

13. The automatic syringe measurement system of claim 9, wherein:

the alignment device is configured to hold between 8 and 25 syringes.

14. The automatic syringe measurement system of claim 9, wherein the processor is further configured to transmit at least one of the imaging data and the plunger depth to an external memory.

* * * * *